(12) United States Patent
Balasubramaniam et al.

(10) Patent No.: US 11,646,032 B2
(45) Date of Patent: May 9, 2023

(54) SYSTEMS AND METHODS FOR AUDIO PROCESSING

(71) Applicant: Medixin Inc., Toronto (CA)

(72) Inventors: Balarajan Balasubramaniam, Toronto (CA); Prasanth Subendran, Karaveddy (LK); Uthayasanker Thayasivam, Colombo (LK); Ketharan Suntharam, Chavakachcheri (LK); Sarangan Janakan, Trincomalee (LK); Kanthasamy Jathusan, Jaffna (LK); Balakrishnan Sathiyakugan, Chavakachcheri (LK)

(73) Assignee: MEDIXIN INC., Kitchener (CA)

( * ) Notice: Subject to any disclaimer, the term of this patent is extended or adjusted under 35 U.S.C. 154(b) by 233 days.

(21) Appl. No.: 17/038,135

(22) Filed: Sep. 30, 2020

(65) Prior Publication Data

US 2021/0272571 A1 Sep. 2, 2021

Related U.S. Application Data

(60) Provisional application No. 62/982,226, filed on Feb. 27, 2020.

(51) Int. Cl.
*G10L 15/26* (2006.01)
*G10L 15/16* (2006.01)
(Continued)

(52) U.S. Cl.
CPC ............ *G10L 15/26* (2013.01); *G06N 3/08* (2013.01); *G10L 15/02* (2013.01); *G10L 15/16* (2013.01); *G16H 10/60* (2018.01); *G16H 80/00* (2018.01)

(58) Field of Classification Search
CPC ......... G06F 40/284; G06F 40/35; G06F 3/16; G06F 3/167; G06N 3/0445; G06N 3/0454;
(Continued)

(56) References Cited

U.S. PATENT DOCUMENTS 9,245,254 B2 * 1/2016 Lord .................. G06Q 10/10
9,584,946 B1 * 2/2017 Lyren .................. G10L 25/81
(Continued)

*Primary Examiner* — Gerald Gauthier
(74) *Attorney, Agent, or Firm* — Own Innovation; James W. Hinton

(57) ABSTRACT

A method of electronically documenting a conversation is provided. The method includes capturing audio of a conversation between a first speaker and a second speaker; generating conversation audio data from the captured audio; and segmenting the conversation audio data into a plurality of utterances according to a speaker segmentation technique. The method further includes, for each utterance: storing time data indicating the chronological position of the utterance in the conversation; passing the utterance to a neural network model, the neural network model configured to receive the utterance as an input and generate a feature representation of the utterance as an output; assigning the utterance feature representation to a first speaker cluster or a second speaker cluster according to a clustering technique; assigning a speaker identifier to the utterance based on the cluster assignment of the utterance; and generating a text representation of the utterance.

18 Claims, 12 Drawing Sheets

(51) Int. Cl.
*G06N 3/08* (2023.01)
*G16H 80/00* (2018.01)
*G16H 10/60* (2018.01)
*G10L 15/02* (2006.01)

(58) Field of Classification Search
CPC .......... G06N 3/08; G06N 20/00; G06N 3/044;
G06N 3/045; G06N 5/04; G06Q 10/10;
G09B 5/02; G10L 15/02; G10L 15/16;
G10L 15/182; G10L 15/22; G10L 15/26;
G10L 17/00; G10L 17/02; G10L 17/04;
G10L 17/18; G10L 21/10; G10L 25/51;
G10L 25/81; G10L 15/04; G10L 15/1815;
G10L 17/08; G10L 17/06; G10L 25/48;
G10L 25/54; G10L 25/63; G10L 25/78;
G10L 25/90; G16H 10/60; G16H 15/00;
G16H 50/20; G16H 80/00; G01N 21/898;
G06V 10/82; G11B 27/102; H04L 65/612
See application file for complete search history.

(56) References Cited

U.S. PATENT DOCUMENTS

| | | | |
|---|---|---|---|
| 9,881,617 B2* | 1/2018 | Sidi | G10L 17/04 |
| 10,002,311 B1* | 6/2018 | Garnavi | G09B 5/02 |
| 10,388,272 B1* | 8/2019 | Thomson | G10L 15/22 |
| 10,580,414 B2* | 3/2020 | Zhang | G10L 25/78 |
| 10,594,757 B1* | 3/2020 | Shevchenko | G06F 40/35 |
| 11,031,013 B1* | 6/2021 | Myers | G10L 15/1822 |
| 11,114,103 B2* | 9/2021 | Zhao | G10L 17/00 |
| 11,132,993 B1* | 9/2021 | McDaniel | G06F 40/284 |
| 11,152,000 B1* | 10/2021 | Myers | G06N 3/0445 |
| 2014/0074467 A1* | 3/2014 | Ziv | G10L 25/51 |
| | | | 704/235 |
| 2014/0074471 A1* | 3/2014 | Sankar | G10L 17/02 |
| | | | 704/E17.001 |
| 2014/0142944 A1* | 5/2014 | Ziv | G10L 17/02 |
| | | | 704/250 |
| 2016/0065637 A1* | 3/2016 | O'Malley | H04L 65/612 |
| | | | 709/231 |
| 2016/0217793 A1* | 7/2016 | Gorodetski | G10L 17/04 |
| 2017/0084295 A1* | 3/2017 | Tsiartas | G10L 17/08 |
| 2018/0174576 A1* | 6/2018 | Soltau | G10L 21/10 |
| 2018/0190305 A1* | 7/2018 | Younger | G11B 27/102 |
| 2018/0308487 A1* | 10/2018 | Goel | G10L 15/1815 |
| 2019/0156832 A1* | 5/2019 | Church | G10L 15/26 |
| 2019/0221317 A1* | 7/2019 | Kempanna | G06N 3/0454 |
| 2019/0341057 A1* | 11/2019 | Zhang | G01N 21/8983 |
| 2020/0126644 A1* | 4/2020 | Polzin | G10L 17/00 |
| 2020/0311354 A1* | 10/2020 | Furukawa | G06F 3/167 |
| 2020/0320135 A1* | 10/2020 | Li | G06F 3/16 |
| 2021/0264909 A1* | 8/2021 | Reece | G06F 40/35 |
| 2021/0264921 A1* | 8/2021 | Reece | G10L 25/48 |
| 2021/0272571 A1* | 9/2021 | Balasubramaniam | G06N 20/00 |
| 2021/0383913 A1* | 12/2021 | Tablan | G10L 15/26 |
| 2022/0199094 A1* | 6/2022 | El Shafey | G10L 15/26 |
| 2022/0343918 A1* | 10/2022 | Fu | H04L 12/1822 |

* cited by examiner

SYSTEMS AND METHODS FOR AUDIO PROCESSING

TECHNICAL FIELD

The following relates generally to audio processing, and more particularly to systems and methods for documenting a conversation using speaker clustering.

INTRODUCTION

Documentation of verbal conversations is a time-consuming but often necessary component of providing assistance or gathering information. Often, the information gathered during such conversations can be of critical importance in determining next steps. In many cases, a verbal conversation is had, and a participant must either split his attention during the conversation by taking notes or rely on an imperfect and incomplete version of the conversation by writing up a recap after the conversation is over. These approaches may produce less reliable artifacts documenting the substance of the conversation and may increase the time required to capture the substance of the conversation in the artifact. Such time requirements can be burdensome on the information gatherer and reduce the amount of time the information gatherer can spend on other parts of his job.

In the medical context, such issues are particularly prevalent. When a patient visits a medical clinic or other healthcare facility, the patient may experience significant wait times. This may be inconvenient for people with busy schedules who have to take time out of their days to make such a visit. Similarly, visits to the doctor can be stressful and the patient may be in some discomfort, which waiting can exacerbate.

For example, a patient may have to wait to see the doctor first in a waiting room, and then may have to wait again in a consultation room for the doctor to arrive. In some cases, patients may interact with more than one healthcare provider (e.g. physician assistant and physician) in sequence, which may add even further waiting.

From the physician's perspective, the physician is going from room to room seeing various patients and having to document each visit. A doctor may visit a patient and then afterwards, before he can advance to the next patient, retreat to an office to type up or otherwise document notes from the previous patient in order to create an artifact of the meeting that can be relied on later. In some cases, a doctor may spend on average 30-45 minutes per patient inputting a diagnosis note or transcription of the consultation. Psychiatric doctors in particular need to complete a lot of documentation, much of which is based off of a template which correlates to Electronic Medical Record ("EMR") system interfaces. Similarly, for general physicians, there are templates that can either be derived or obtained from these EMR to summarize or narrate and input notes into the EMR for physicians to review, which may reduce the time from 30 minutes to a couple of minutes on average.

The significant time spent per patient documenting consultations can have negative effects including reducing the number of patients that a doctor can see in a given time period and adds significant administrative burden to the doctor that is not stimulating and detracts from their ability to use their skills to assist patients.

Accordingly, there is a need for an improved system and method for documenting conversations that overcomes at least some of the disadvantages of existing systems and methods.

SUMMARY

A method of electronically documenting a conversation is provided. The method includes: capturing audio of a conversation between a first speaker and a second speaker; generating conversation audio data from the captured audio; segmenting the conversation audio data into a plurality of utterances according to a speaker segmentation technique; for each utterance: storing time data indicating the chronological position of the utterance in the conversation; passing the utterance to a neural network model, the neural network model configured to receive the utterance as an input and generate a feature representation of the utterance as an output; assigning the utterance feature representation to a first speaker cluster or a second speaker cluster according to a clustering technique; assigning a speaker identifier to the utterance based on the cluster assignment of the utterance; generating a text representation of the utterance; generating a digital transcript of the conversation by chronologically ordering the text representations of the utterances according to the time data for the utterances; and importing the digital transcript into an electronic conversation artifact.

The first speaker may be a healthcare professional and the second speaker may be a patient. The conversation may be a medical consultation.

The electronic conversation artifact may be an electronic medical record.

The neural network model may include a convolutional neural network.

A method of generating and delivering an electronic prompt to a speaker during a conversation is also provided. The method includes: capturing audio of a conversation between a first speaker and a second speaker; generating conversation audio data from the captured audio; segmenting the conversation audio data into a plurality of utterances according to a speaker segmentation technique; transcribing the utterance audio data to utterance text data; analyzing the utterance text data to determine an utterance subject matter; generating a prompt using the utterance subject matter; and displaying the prompt at an information gatherer device.

The utterance text data may be analyzed using a text classifier.

A system for processing audio via speaker clustering is also provided. The system includes: an audio capture device configured to capture audio of a conversation between a first speaker and a second speaker and generate conversation audio data from the captured audio; an audio processing server communicatively connected to the audio capture device, the audio processing server configured to: receive the conversation audio data from the audio capture device; segment the conversation audio data into a plurality of utterances, each utterance comprising utterance audio data, according to a segmentation technique; and process the plurality of utterances via a speaker clustering pipeline, including: passing each utterance to a neural network model, the neural network model configured to generate a feature representation of the utterance; passing the feature representation to a cluster model, the cluster model configured to assign the feature representation to a cluster based on speaker identity; and storing the cluster assignment in a memory of the audio processing server.

The audio processing server may be configured to generate a text representation of at least one utterance.

The audio processing server may be configured to generate a digital transcript of the conversation including text representations of two or more utterances.

The system may include an information gatherer device communicatively connected to the audio processing server via a network, the information gatherer device configured to display the digital transcript for review by a user.

Upon approval of the digital transcript, the digital transcript may be automatically imported into an electronic conversation artifact.

The system may include an electronic conversation artifact server communicatively connected to the audio processing server via the network. The electronic artifact server may be configured to generate and store the electronic conversation artifact.

The neural network model may be a VGGish model.

The speaker clustering pipeline may include extracting time series data of the utterance audio data.

The time series data may be extracted using a librosa library.

The speaker clustering pipeline may include extracting mel features using an FFT window function.

The FFT window function may have a window length of 25 ms.

The window function may have a hop length of 10 ms.

Each window data may have 64 mel frequencies extracted therefrom.

The speaker clustering pipeline may include creating a two-dimensional spectrogram frame from the feature representation. The two-dimensional spectrogram frame may be used as a unit input for the neural network model.

The neural network model may be configured to receive an input comprising a two-dimensional spectrogram frame.

The two-dimensional spectrogram frame may have a pixel size of 64×96.

The utterance data may be provided to the neural network model as a batch of spectrogram frames.

The number of frames in the batch may be determined by the time length of the utterance audio data.

The clustering technique may be dominant sets and cosine distance may be used as a distance metric.

The cluster model may implement a similarity function for determining the cluster assignment.

The similarity function may use cosine distance.

The clustering technique may include at least one of dominant sets, k-means, spectral clustering, and hierarchical clustering.

The audio processing server may include a speaker identification subsystem including a convolutional neural network and an attention-based LSTM layer.

The convolutional neural network may be SincNet.

In an aspect, the present disclosure provides a new tensor flow model (VGGish) that may have improved performance over state-of-the-art models, such as Visual Geometry Group (VGGVox). The model may have improved performance compared to VGGVox for the metric of misclassification rate.

In another aspect, a model trained for common speaker casualties may be transferred to Speaker clustering.

In another aspect, the present disclosure provides systems and methods which apply transfer learning on a modified VGGish audio classification model to extract deep audio embeddings. The modified model may outperform VGGVox speaker clustering results on studio quality datasets and noisy datasets. The improvements may include improvement in pure speaker clustering capability apart from application-dependent nuisances.

In an aspect, the present disclosure provides systems and methods for performing speaker clustering and/or speaker identification which are primarily on robust high-level feature extraction of voice.

In another aspect, the present disclosure provides a speaker identification system which uses an Attention-based LSTM architecture which may help extract high-level features with a smaller amount of data while providing higher accuracy.

In another aspect, the present disclosure provides a speaker clustering system which uses transfer learning to produce a robust generalized model that may be capable of adapting to new languages and new accents.

In an embodiment, the speaker clustering system may use a transfer learning approach. The speaker clustering system may perform a deep feature extracting technique that is capable of producing a unified model for multi-language multi accent speaker clustering that is robust to noise. Transferring deep features from audio processing problems to voice problems may be used to build such a highly generalized model.

In another embodiment, batch normalization may be used. Batch normalization may be used in contrast to existing approaches to achieve a low internal covariant shift and create more viable activation functions which results in higher order generalization. A couple deeper networks may capture the fine-grained deep features which help the clustering to perform well on multiple domains. The proposed approach may provide a unified model for speaker clustering in a multi-language, multi accent setup. The proposed approach may outperform prior approaches in both in-domain and out-domain. The model may be robust to noise. Further, test data may include multi-accent and multi-language setups and noisy data set.

In an aspect, the speaker clustering system provided herein may outperform existing approaches. For example, the speaker clustering system may outperform VGGVox-based speaker clustering results on studio quality datasets by 48% and in noisy datasets by 42% conforms a better generalization and adaptability.

Other aspects and features will become apparent, to those ordinarily skilled in the art, upon review of the following description of some exemplary embodiments.

BRIEF DESCRIPTION OF THE DRAWINGS

The drawings included herewith are for illustrating various examples of articles, methods, and apparatuses of the present specification. In the drawings.

DETAILED DESCRIPTION

Various apparatuses or processes will be described below to provide an example of each claimed embodiment. No embodiment described below limits any claimed embodiment and any claimed embodiment may cover processes or apparatuses that differ from those described below. The claimed embodiments are not limited to apparatuses or processes having all of the features of any one apparatus or process described below or to features common to multiple or all of the apparatuses described below.

One or more systems described herein may be implemented in computer programs executing on programmable computers, each comprising at least one processor, a data storage system (including volatile and non-volatile memory and/or storage elements), at least one input device, and at least one output device. For example, and without limitation, the programmable computer may be a programmable logic unit, a mainframe computer, server, and personal computer, cloud-based program or system, laptop, personal data assistance, cellular telephone, smartphone, or tablet device.

Each program is preferably implemented in a high-level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device readable by a general or special purpose programmable computer for configuring and operating the computer when the storage media or device is read by the computer to perform the procedures described herein.

A description of an embodiment with several components in communication with each other does not imply that all such components are required. On the contrary, a variety of optional components are described to illustrate the wide variety of possible embodiments of the present invention.

Further, although process steps, method steps, algorithms or the like may be described (in the disclosure and/or in the claims) in a sequential order, such processes, methods and algorithms may be configured to work in alternate orders. In other words, any sequence or order of steps that may be described does not necessarily indicate a requirement that the steps be performed in that order. The steps of processes described herein may be performed in any order that is practical. Further, some steps may be performed simultaneously.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

Figure 1:
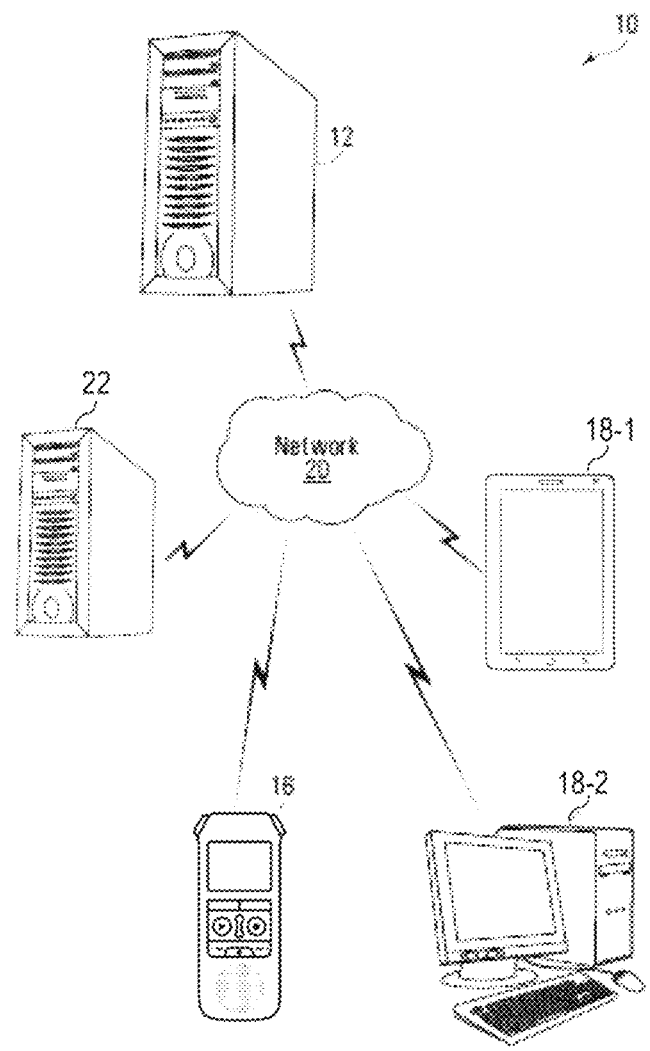
FIG. 1 is a schematic diagram of an audio capture and processing system, according to an embodiment.

Referring now to FIG. 1, shown therein is a block diagram illustrating an audio capture and processing system 10, in accordance with an embodiment.

The systems of the present disclosure perform speaker clustering. The system includes a speaker clustering model that may have improved results over existing state-of-the-art models such as Visual Geometry Group (VGGVox). The system may include a new tensor flow model (VGGish) that has shown improved performance as compared to VGGVox results.

The model may use a transfer learning approach, such as by transferring a model trained for common speaker casualties to speaker clustering.

Experiments were performed to test the model and approaches on TIMIT (Texas Instruments Massachusetts Institute of Technology) and VCTK (Voice Cloning Toolkit) datasets, and achieve state of the art achieved improved results compared to VGG Vox for the metric of Misclassification Rate (MR).

The system 10 can be used to electronically document a conversation between an information gatherer and an information provider. Generally, the information gatherer may have a responsibility to document the substance of the conversation. In some cases, the responsibility to document may include a legal or regulatory obligation. The meeting between the information gatherer and the information provider may be initiated by the gatherer or the provider. The information gatherer may be a healthcare provider (e.g. doctor, nurse, physician assistant), an emergency worker (e.g. police officer), a social worker, a psychiatrist or other mental health professional, forensic personnel, or the like. The information provider may be a patient, witness, victim, client, etc.

The system 10 may process received audio data and generate a prompt. In some cases, the system 10 can generate and present a prompt to an information gatherer through analyzing the substance of a conversation in real-time. The prompt may be a suggested action or consideration and may help the information gatherer manage the conversation and improve information gathering. In an example, a physician or other healthcare professional consulting with a patient may be presented with a prompt by the system 10 related to the subject matter of the conversation. The prompt may help guide the physician more efficiently through the consultation.

For example, a computer system for processing audio of a conversation (e.g. computer system of FIG. 3, described below) may include software components configured to generate prompts based on the processed audio and output the prompt in a suitable format (e.g. via utterance analyzed 346, prompt generator module 350 of FIG. 3, below). The prompt contains information that may be useful to a recipient of the prompt and may inform subsequent action. The prompt recipient may be a conversation participant or a third party (i.e. not a conversation participant). The prompt is determined based on the processed audio data. The prompt may be outputted to a prompt recipient in any suitable format, such as a visual output on a device (e.g. text or other visual representation) or an audio output (e.g. audio message, signal) via a device speaker. The prompt may be provided to the recipient as a text or graphical message. The message may be an SMS message or the like on a mobile device, an email, a message in an application user interface, or other electronic message format. In an example, the prompt recipient may be a conversation participant (e.g. a speaker) and the prompt may be displayed on a device of the conversation participant. In another example, the prompt recipient may be a third party and the prompt may be transmitted to a device of the third party (not shown in FIG. 1, but may be connected to the audio processing server 12 via a network connection) where the prompt can be outputted to the third party as a message in visual, audio, or other suitable format.

The prompt may include a suggestion or recommendation to the recipient. In some cases, the prompt may be used to manage a conversation, or the information gathered or to be gathered therefrom, such as by directing lines of inquiry or providing considerations. In some cases, the prompt may indicate or suggest a subsequent action to be taken, such as by the prompt recipient or other party.

The system 10 includes an audio processing server platform 12, which communicates with an audio capture device 16, information gatherer devices 18-1 and 18-2, and an electronic conversation artifact server 22 via a network 20. The information gatherer devices 18-1 and 18-2 are referred to herein collectively as information gatherer devices 18 and generically as information gatherer device 18. The information gathering devices 18 are associated with an information gatherer. The information gatherer devices 18 may be any suitable computing device. In FIG. 1, information gatherer device 18-1 is depicted as a mobile device (tablet) and information gatherer device 18-2 is depicted as a workstation or desktop. The mobile information gathering device 18-1 may advantageously be used by the information gatherer during the conversation and taken easily from one conversation location to another.

The server platform 12, and devices 16, 18, 22 may be a server computer, desktop computer, notebook computer, tablet, PDA, smartphone, or another computing device. The devices 12, 16, 18, 22 may include a connection with the network 20 such as a wired or wireless connection to the Internet. In some cases, the network 20 may include other types of computer or telecommunication networks. The network 20 may be a secure network configured to securely transmit personal health information or other confidential information in accordance with established laws or standards. The devices 12, 16, 18, 22 may include one or more of a memory, a secondary storage device, a processor, an input device, a display device, and an output device. Memory may include random access memory (RAM) or similar types of memory. Also, memory may store one or more applications for execution by processor. Applications may correspond with software modules comprising computer executable instructions to perform processing for the functions described below. Secondary storage device may include a hard disk drive, floppy disk drive, CD drive, DVD drive, Blu-ray drive, or other types of non-volatile data storage. Processor may execute applications, computer readable instructions or programs. The applications, computer readable instructions or programs may be stored in memory or in secondary storage or may be received from the Internet or other network 20.

Input device may include any device for entering information into device 12, 16, 18, 22. For example, input device may be a keyboard, keypad, cursor-control device, touch-screen, camera, or microphone. Display device may include any type of device for presenting visual information. For example, display device may be a computer monitor, a flat-screen display, a projector or a display panel. Output device may include any type of device for presenting a hard copy of information, such as a printer for example. Output device may also include other types of output devices such as speakers, for example. In some cases, device 12, 16, 18, 22 may include multiple of any one or more of processors, applications, software modules, second storage devices, network connections, input devices, output devices, and display devices.

Although devices 12, 16, 18, 22 are described with various components, one skilled in the art will appreciate that the devices 12, 16, 18, 22 may in some cases contain fewer, additional or different components. In addition, although aspects of an implementation of the devices 12, 16, 18, 22 may be described as being stored in memory, one skilled in the art will appreciate that these aspects can also be stored on or read from other types of computer program products or computer-readable media, such as secondary storage devices, including hard disks, floppy disks, CDs, or DVDs; a carrier wave from the Internet or other network; or other forms of RAM or ROM. The computer-readable media may include instructions for controlling the devices 12, 16, 18, 22 and/or processor to perform a particular method.

Devices such as server platform 12 and devices 16, 18, 22 can be described performing certain acts. It will be appreciated that any one or more of these devices may perform an act automatically or in response to an interaction by a user of that device. That is, the user of the device may manipulate one or more input devices (e.g. a touchscreen, a mouse, or a button) causing the device to perform the described act. In many cases, this aspect may not be described below, but it will be understood.

As an example, it is described below that the devices 16, 18, 22 may send information to the server platform 12. For example, a user using the device 18 may manipulate one or more inputs (e.g. a mouse and a keyboard) to interact with a user interface displayed on a display of the device 18. Generally, the device 18 may receive a user interface from the network 20 (e.g. in the form of a webpage). Alternatively, or in addition, a user interface may be stored locally at a device (e.g. a cache of a webpage or a mobile application).

Server platform 12 may be configured to receive a plurality of information, from each of the plurality of devices 16, 18 and the server 22.

In response to receiving information, the server platform 12 may store the information in storage database. The storage may correspond with secondary storage of the devices 16, 18 and the server 22. Generally, the storage database may be any suitable storage device such as a hard disk drive, a solid-state drive, a memory card, or a disk (e.g. CD, DVD, or Blu-ray etc.). Also, the storage database may be locally connected with server platform 12. In some cases, storage database may be located remotely from server platform 12 and accessible to server platform 12 across a network for example. In some cases, storage database may comprise one or more storage devices located at a networked cloud storage provider.

The audio capture device 16 is a device configured to capture audio of the conversation between the information gatherer and information provider and generate audio data comprising a digital representation of the conversation. The audio capture device 16 may include a recording device such as a microphone, an audio data generating subsystem for generating audio data from an audio signal, and a communication subsystem for transmitting the audio data to the audio processing server 12.

In some cases, the audio capture device 16 may be a physically separate device from the information gatherer device 18 designated for capturing audio. In other cases, the audio capture device 16 may be a component of the information gatherer device 18.

The electronic conversation artifact server 22 is configured to generate, store, and manipulate electronic conversation artifacts such as an electronic medical record. The server 22 may implement a server-side component of an electronic artifact management system. The server-side component may interact with a client-side component of the electronic artifact management system implemented at the information gatherer device 18.

The server platform 12 may be a purpose-built machine designed specifically for processing audio data via machine learning techniques such as clustering. In particular, the server platform 12 may process audio data of a conversation via speaker clustering to generate a digital transcript of the conversation that may be incorporated into an electronic conversation artifact stored at the electronic artifact server 22. The server 12 may process the audio data to generate and present prompts to the information gatherer at the information gatherer device 18 in real-time as the conversation is taking place.

Generally, the server 12 receives audio data of a conversation from the audio capture device 16, processes the audio data into speaker-homogeneous components or clusters, and generates a transcript of the conversation using the output of the audio processing task. Processing the audio data includes segmenting the audio data into a plurality of speaker utterances and allocating the speaker utterances, via a clustering technique, to a set of components where each component contains utterances from a unique speaker. The number of components (clusters) is equal to the number of unique speakers in the utterance set.

Figure 2:
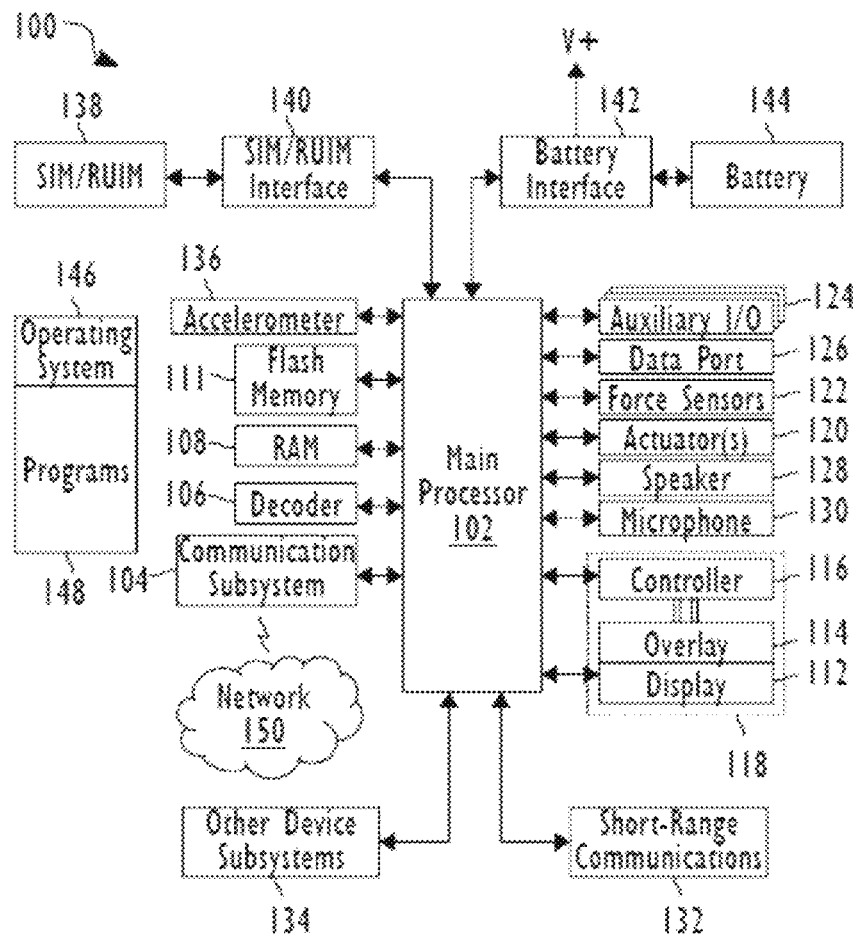
FIG. 2 is a block diagram of a computing device.

FIG. 2 shows a simplified block diagram of components of a device 1000, such as a mobile device or portable electronic device. The device 1000 may be, for example, any of devices 12, 16, 18, 22 of FIG. 1.

The device 1000 includes multiple components such as a processor 1020 that controls the operations of the device 1000. Communication functions, including data communications, voice communications, or both may be performed through a communication subsystem 1040. Data received by the device 1000 may be decompressed and decrypted by a decoder 1060. The communication subsystem 1040 may receive messages from and send messages to a wireless network 1500.

The wireless network 1500 may be any type of wireless network, including, but not limited to, data-centric wireless networks, voice-centric wireless networks, and dual-mode networks that support both voice and data communications.

The device 1000 may be a battery-powered device and as shown includes a battery interface 1420 for receiving one or more rechargeable batteries 1440.

The processor 1020 also interacts with additional subsystems such as a Random Access Memory (RAM) 1080, a flash memory 1100, a display 1120 (e.g. with a touch-sensitive overlay 1140 connected to an electronic controller 1160 that together comprise a touch-sensitive display 1180), an actuator assembly 1200, one or more optional force sensors 1220, an auxiliary input/output (I/O) subsystem 1240, a data port 1260, a speaker 1280, a microphone 1300, short-range communications systems 1320 and other device subsystems 1340.

In some embodiments, user-interaction with the graphical user interface may be performed through the touch-sensitive overlay 1140. The processor 1020 may interact with the touch-sensitive overlay 1140 via the electronic controller 1160. Information, such as text, characters, symbols, images, icons, and other items that may be displayed or rendered on a portable electronic device generated by the processor 102 may be displayed on the touch-sensitive display 118.

The processor 1020 may also interact with an accelerometer 1360 as shown in FIG. 1. The accelerometer 1360 may be utilized for detecting direction of gravitational forces or gravity-induced reaction forces.

To identify a subscriber for network access according to the present embodiment, the device 1000 may use a Subscriber Identity Module or a Removable User Identity Module (SIM/RUIM) card 1380 inserted into a SIM/RUIM interface 1400 for communication with a network (such as the wireless network 1500). Alternatively, user identification information may be programmed into the flash memory 1100 or performed using other techniques.

The device 1000 also includes an operating system 1460 and software components 1480 that are executed by the processor 1020 and which may be stored in a persistent data storage device such as the flash memory 1100. Additional applications may be loaded onto the device 1000 through the wireless network 1500, the auxiliary I/O subsystem 1240, the data port 1260, the short-range communications subsystem 1320, or any other suitable device subsystem 1340.

For example, in use, a received signal such as a text message, an e-mail message, web page download, or other data may be processed by the communication subsystem 1040 and input to the processor 1020. The processor 1020 then processes the received signal for output to the display 1120 or alternatively to the auxiliary I/O subsystem 1240. A subscriber may also compose data items, such as e-mail messages, for example, which may be transmitted over the wireless network 1500 through the communication subsystem 1040.

For voice communications, the overall operation of the portable electronic device 1000 may be similar. The speaker 1280 may output audible information converted from electrical signals, and the microphone 1300 may convert audible information into electrical signals for processing.

Figure 3:
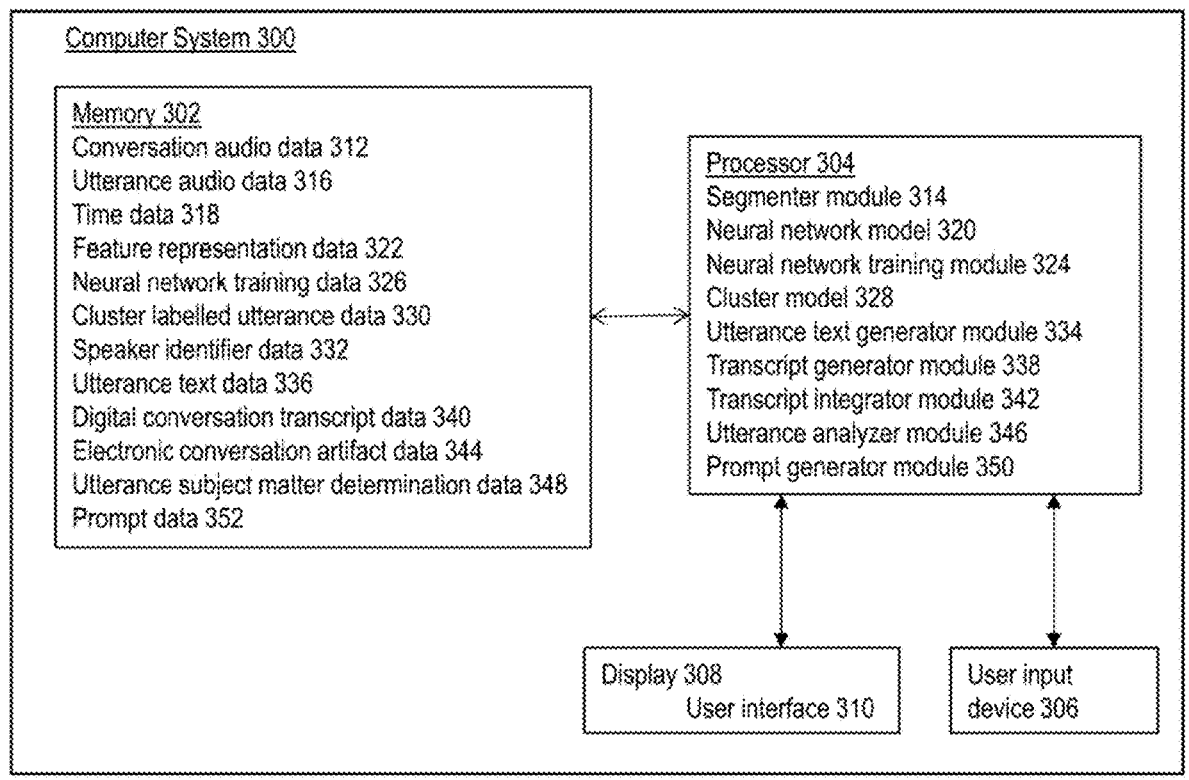
FIG. 3 is a block diagram of a computer system for processing audio of a conversation, according to an embodiment.

Referring now to FIG. 3, shown therein is a computer system 300 for processing audio of a conversation, according to an embodiment.

The computer system 300 can process received audio data of a conversation and generate a transcript of the conversation. The audio data may be received from the audio capture device 16 of FIG. 1.

The computer system 300 may process received audio data and generate a prompt, which can be provided to and used by a recipient.

The system 300 includes a memory 302 in communication with a processor 304.

The memory 302 stores various data that may be received, manipulated, or generated by the system 300. The memory 302 may be stored at any one or more of an audio processing server (e.g. server 12 of FIG. 1), a conversation participant device (e.g. information gatherer device 18 of FIG. 1), and an electronic conversation artifact server (e.g. server 14 of FIG. 1).

The processor 304 is configured to execute a plurality of software modules including computer-implemented instructions that, when executed, cause the system 300 to perform actions, operations, and functions described herein. The processor 304 may be located at the server 12, information gatherer device 18, or artifact server 14.

The system 300 includes a user input device 306 which may be located at the information gatherer device 18. The user input device 306 receives user input from a conversation participant (speaker) such as a healthcare professional.

The system 300 includes a display 308 which may be located at the information gatherer device 18. The display 308 displays a user interface 310 for facilitating user interaction with the system 300.

The memory 302 stores conversation audio data 312. The conversation audio data 312 may be an audio file in any suitable audio file format. The conversation audio data 312 may be received from an audio capture device, such as audio capture device 16 of FIG. 1. The conversation audio data 312 may be received and processed as an audio stream or batch. The conversation audio data 312 may be received from the audio capture device 16 via a communication interface of the system 300. The conversation audio data 312 includes a plurality of utterances from a plurality of speakers.

The conversation audio data 312 comprises a digital representation of the audio of a conversation. The conversation is a verbal exchange between two or more speakers. The speakers may include an information gatherer and one or more information providers. The information gatherer may be a healthcare provider (e.g. physician, nurse), police officer, social worker, or the like. The information provider may be a patient, witness, victim, or the like. In some cases, the conversation may include additional information providers (a secondary information provider) such as a parent, guardian, adult child, etc. that may participate in the conversation to assist and facilitate provision of information from the primary information provider to the information gatherer.

The conversation may be a consultation. The consultation may be a medical consultation, such as between a patient and healthcare provider. The conversation may be any interaction between two parties in which one party is responsible for documenting the conversation as part of a formal recording process. Once such example may be a police statement between a police officer and a witness, victim, suspect, or other information provider.

The conversation audio data 312 is fed to a segmenter module 314 which is located at the processor 304. The segmenter module 314 generates a plurality of utterances by segmenting the audio data 312 into speaker segments.

The segmenter module 314 generates utterances according to a speaker segmentation technique. The segmentation technique may include speaker change detection. Speaker change detection may include detecting speaker change points in the audio data 312 and portioning the audio data 312 according to the speaker change points. The segmenter module 314 may use audio characteristics to determine speaker change points. The segmenter module 314 may generate utterances comprising acoustically homogeneous segments.

The utterances are stored in memory 302 as utterance audio data 316. An utterance comprises a unit of speech corresponding to some portion of the recorded conversation. The utterance includes a single speaker (i.e. speaker homogeneous). Utterances may be of variable length.

Each utterance includes time data 318 associated therewith which is stored in memory 302.

The time data 318 indicates the chronological position of the utterance in the conversation. Certain time data 318 may be included with the conversation audio data 312. For example, the audio capture device 16 may be configured to generate conversation audio data 312 that includes time metadata.

The time data 318 may include an utterance start time and/or an utterance end time. The time data 318 may include a time label or value that indicates the chronological position of the utterance. For example, a conversation having 'n' utterances may have time labels 1, 2, 3, . . . , n, where 1 corresponds to the first utterance (chronologically) and n to the nth utterance. The time label may be determined from the utterance start or end time.

The utterance audio data 316 for a given utterance is fed to a trained neural network model 320. The neural network model 320 is located at processor 304.

Figure 8:
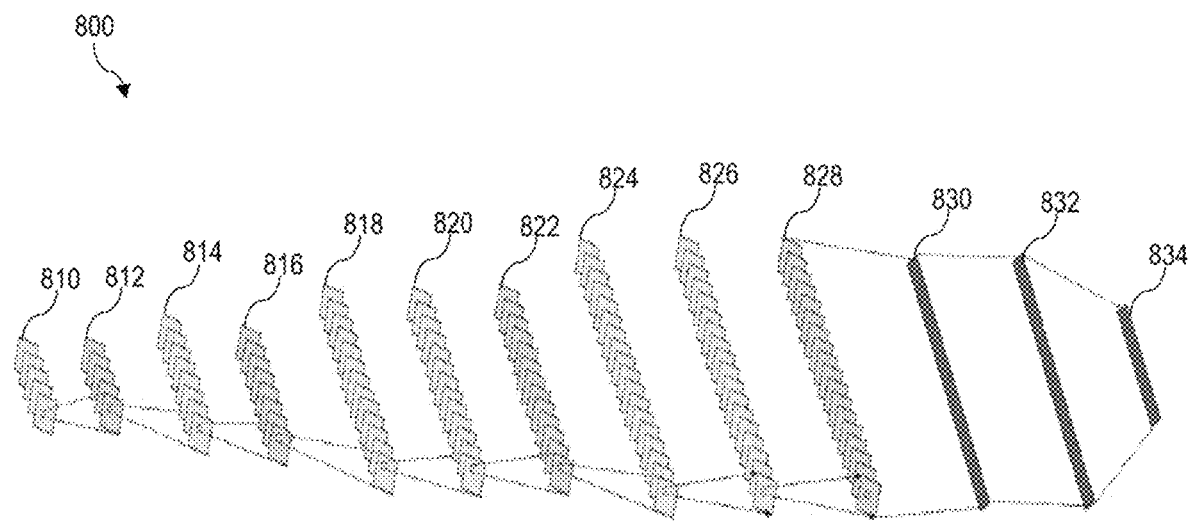
FIG. 8 is a model architecture of a convolutional neural network (CNN) for generating audio feature representations as part of a speaker clustering process, according to an embodiment.

The neural network model 320 may act as an embedding extractor. The neural network 320 may be a convolutional neural network ("CNN"). In an embodiment, the neural network model 320 may have an architecture as shown in FIG. 8.

The neural network model 320 is configured to receive utterance audio data 316 as an input and generate a feature representation 322 of the utterance as an output. The feature representation 322 is stored in memory 302. The feature representation 322 may comprise an m-dimensional feature vector.

The neural network model 320 may be a tensor flow model. The neural network model 320 may be built on a VGG backbone.

The neural network model 320 may be a VGGish model.

The network model 320 may outperform existing models and approaches. The neural network model 320 may be a network trained using a transfer learning process. The neural network model 320 may include a network trained for common speaker casualties transferred to speaker clustering via transfer learning.

The neural network model 320 may provide improved results for misclassification metric (MR) over existing approaches. The neural network model 320 may shown an improvement in pure speaker clustering capability apart from application-dependent nuisances over existing approaches. The neural network model 320 may learn large-scale audio classification tasks.

The neural network model 320 may include a generic audio embedding model. The generic audio embedding model may differentiate a wide range of voice characteristics and capture acoustic and linguistic content. The neural network model 320 may include a large-scale audio classification model such as AlexNet, VGG, Inception, or ResNet.

The neural network model 320 is trained using a neural network training module 324. The neural network training module 324 is stored at the processor 304.

The neural network training module 324 implements a neural network training process. The training process may be a supervised learning process.

The neural network training module 324 uses neural network training data 326 which is stored in memory 302. The neural network training data 326 is provided as input to the neural network training module 324 and used to generate the neural network model 320 as an output.

In a supervised learning process, both the inputs and the outputs are provided. The network processes the inputs and compares resulting outputs against the desired outputs. Errors are propagated back through the system, causing the system to adjust the weights which control the network. This process occurs over and over as the weights are continually tweaked. The neural network training data 326 enables the training. During the training of a network the same set of training data 326 may be processed many times as the connection weights are refined.

The feature representation 322 is fed to a cluster model 328. The cluster model 328 is located at the processor 304.

The cluster model 328 includes a plurality of clusters. The cluster model 328 assigns the utterance, based on the feature representation 322, to a cluster according to a clustering technique. In doing so, the cluster model 328 generates a cluster assignment or label for the utterance which can differentiate utterances from one speaker in the conversation from utterances of the other speakers in the conversation. The labelled utterance (or cluster assignment) 330 is stored in memory 302.

The clusters correspond to different speakers in the conversation. For example, the system 300 may process a conversation having a first speaker (e.g. a doctor) and a second speaker (e.g. a patient) where the cluster model 328 is configured to assign utterances (using their feature representations 322) from the first speaker to a first cluster and utterances from the second speaker to a second cluster. Accordingly, the clusters represent speaker homogenous components or groupings of utterances from the conversation.

The cluster model 328 may use any suitable clustering technique such as hierarchical clustering, spectral clustering, dominant sets, k-means, or the like.

The cluster model 328 may perform cluster assignment based on a distance or similarity function. In an embodiment, the similarity function may use cosine distance.

In an example, the clustering technique is dominant sets. Dominant sets is a graph-based clustering algorithm. Dominant set clustering is a graph-based method that generalizes the problem of finding a maximal clique to edge-weighted graphs. A natural application of this method is for partitioning (clustering) a graph into disjoint sets. In this framework, a dataset is modeled as an undirected edge-weighted graph $G=(V, E, w)$ with no self loops, in which the nodes V are the items of the dataset (represented by feature vectors). The edges $E \subseteq V \times V$ are the pairwise relations between nodes and their weight function $\omega: E \rightarrow R \geq 0$ calculates pairwise similarities.

A distance matrix for given embeddings can be computed using the cosine distance to construct a similarity function. Cosine distance may provide good performance on speaker classification tasks. Given two utterances and their m-dimensional feature vectors $f_i$ and $f_j$, the following function can be applied:

$$\omega(f_i, f_j) = \exp\left\{-\frac{d(f_i, f_j)}{\sigma}\right\}$$

In the above function, d is the cosine distance between given features and a is the similarity scaling parameter.

We formulated $\sigma = \sigma_i \cdot \sigma_j$ where the similarity scaling factor depends on local neighborhoods of given features $f_i$ and $f_j$ and it is determined as follows:

$$\sigma_i = \frac{1}{|N_i|} \sum_{k \in N_i} d(f_i, f_k)$$

In the above function, Ni represents the nearest neighborhood of element i. In an embodiment, $|Ni|=7$.

Upon assigning a feature representation 322 to a cluster, a label may be applied to the feature representation 322 and to the utterance (e.g. utterance audio data 316) represented by the feature representation 322. The label may be applied to all feature representations 322 assigned to the same cluster.

The cluster label may be generic and non-descriptive, such as cluster 1, cluster 2, etc., or speaker 1, speaker 2, etc. The cluster label may then be used to generate a speaker identifier (speaker ID) 332. The speaker ID 332 is a descriptive label for utterances of the same cluster. The speaker IDs may be used to generate a transcript in which utterances are attributed to a particular speaker. Example speaker IDs may include patient and physician, or John Doe (patient) and Dr. Smith (physician).

In an embodiment, the speaker IDs 332 may be provided by the information gatherer via the user interface 310 prior to or after the conversation. The system 300 may automatically assign the speaker IDs 332 to the labeled utterances 330 based on the cluster assignment. In other cases, the information gatherer user may manually relabel labeled utterances 330 with speaker ID 332 to generate a more descriptive transcript.

In some cases, the cluster label assigned by the cluster model 328 upon clustering may be a speaker identifier 332.

The cluster model 328 may include a classifier configured to treat labels assigned during clustering as classes. For example, the classifier may predict a class for the utterance based on the feature representation 322.

Utterance audio data 316 is fed to an utterance text generator 334. The utterance text generator 334 is located at the processor 304.

The utterance text generator 334 generates an utterance text 336 comprising a text representation of the utterance from the utterance audio data 316. The utterance text 336 is stored in memory 302.

The utterance text generator 334 may be configured to generate a text file (or other text representation) from an audio file. The utterance text generator 334 may use speech-to-text software to generate the utterance text 336.

The utterance text 336 is fed to a transcript generator 338 which is located at the processor 304. The transcript generator 338 also receives time data 314 and speaker ID 332 for the given utterance text 336. In some cases, the speaker ID 332 may be attributed to utterance text 336 as part of the utterance text generation process carried out by the utterance text generator 334.

The transcript generator 338 generates a digital transcript 340 from the utterance text 336 of a plurality of utterances. The digital transcript 340 is a text representation of the conversation that includes two or more utterances. In this sense, the conversation transcript 340 may cover a portion of the conversation or the entire conversation.

To create the transcript 340, the transcript generator 338 may arrange the utterance text 336 in chronological order using the time data 314. The transcript generator 338 may also include instructions for the presentation of the transcript 340 according to a desired format, such as where each subsequent utterance is presented on a new line to increase readability. For example, a portion of the transcript 340 may look like this:

Speaker 1: [utterance text]
Speaker 2: [utterance text]
Speaker 1: [utterance text]

The processor 304 also includes a transcript integrator module 342. The transcript integrator module 342 receives the conversation transcript 340 and integrates the transcript 340 into an electronic conversation artifact 344. In some embodiments, this process may be performed automatically by the system 300.

The electronic conversation artifact 344 may be stored at the server 22 of FIG. 1. The electronic conversation artifact 344 may be generated via an artifact generator module which may be located at the electronic artifact server 22 of FIG. 1. The artifact generator module may be part of an electronic artifact management system operating at the electronic artifact server 22 and the information gatherer device 18.

The electronic conversation artifact 344 may be an electronic medical report (EMR), a police report (e.g. witness report, victim statement, etc.), or the like. The electronic conversation artifact 344 may be a formal electronic representation of the conversation having a predefined format and that includes certain mandated or required information about the encounter for documentation and record keeping purposes. Different types of artifacts 344 may have different required information and different formats.

In many cases, industry-specific electronic conversation artifact management systems such as EMR systems may already be in use. Accordingly, the transcript integrator 342 may be configured to operate in conjunction with such existing software systems by facilitating the import of the transcript 340 into the conversation artifact 344 including any necessary format conversion.

The transcription integrator module 342 may allow a user to select what portions of the transcript goes into the artifact 344 (e.g. an excerpt). In some cases, such as where full documentation of the conversation is critical or required, the whole transcript 340 may automatically be imported into the artifact 344.

The transcript integrator module 342 may allow a user to edit or add content to the artifact 344 that is related to the transcription 340, such as annotations or notes.

The transcript integrator module 342 provides a visual display of the transcription 340 to be integrated into the artifact 340 for approval by a reviewer (e.g. the information gatherer, such as a documenting physician).

The transcript integrator module 342 may be configured to convert the transcript 340 into another format that is accepted by the artifact management system prior to importing the transcript 340 into the artifact 344.

The system 300 is also configured to analyze utterance data (utterance audio data 316 or utterance text 336), determine a subject matter or topic that has been discussed, and generate a suggestion or recommendation to the information gatherer that can be presented via the user interface 310 at the information gatherer device 18.

The processor 304 includes an utterance analyzer 346. The utterance analyzer 346 receives an utterance (e.g. utterance text 336 or utterance audio data 316) and analyzes the utterance to detect one or more subject matters or topics of the utterance. In a medical context, detected topics may include a particular disease, or a potential diagnosis, treatment, prescription, referral, prognosis, etc. The utterance may be utterance audio data 316 or utterance text data 336.

The utterance analyzer 346 uses machine learning to generate a subject matter determination 348. In an embodiment, the utterance analyzer 346 may include a machine learning model (e.g. a trained classifier) configured to receive an utterance as an input and generate a subject matter determination (e.g. classification) as an output.

In an embodiment, the utterance analyzer 346 includes a text classifier configured to perform text classification on utterance text data 336 to identify a subject matter.

The utterance analyzer 346 may analyze all utterances or a subset of utterances. The subset may include a single utterance, commonly labelled utterances (i.e. utterances from a particular speaker, such as a patient), or a conversation transcript 340.

The utterance analyzer 346 may be configured to analyze utterance text 336 or some other digital representation of the utterance (e.g. audio data of the utterance).

The utterance analyzer 346 receives the utterance text 336 as an input, analyzes the utterance text 336 for subject matter and outputs one or more utterance subject matters or topics 348.

The utterance subject matter 348 is fed to a prompt generator 350. The prompt generator 350 is located at the processor 304.

The prompt generator 350 is configured to generate a subject-matter related prompt 352 based on the utterance subject matter 348. The prompt 352 is presented to the information gatherer via visual (e.g. text) or auditory presentation. For a visual prompt, the prompt 352 is displayed via the user interface 310 at the information gatherer device 18. Visual presentation of the prompt 352 may advantageously provide discreet presentation and assistance to the information gatherer without knowledge of the information provider.

Prompts 352 may be stored in a prompt database. The prompt 352 may be linked in the prompt database to an utterance subject matter 348 such that inputting or querying a particular utterance subject matter 348 returns a prompt for that utterance subject matter 348. Generally, the utterance subject matter determination 348 is descriptive enough to allow a meaningful prompt 352 to be identified and displayed to the information gatherer.

The prompt 352 may be a suggestion or a question. The prompts 352 may be designed to assist the information gatherer navigate the conversation and/or analyze the information provided by the information provider. For example, in a medical context the utterance analyzer 346 may analyze the utterance text 336 and detect that disease X (i.e. utterance subject matter 348) has been discussed. The utterance subject matter 348 of disease X is provided to the prompt generator 350 which generates a prompt 352 comprising a suggestion "have you considered prescribing drug Y?"

In some embodiments, the utterance analyzer 346 may include a machine learning model configured to receive an utterance as input and output a prompt. The prompt outputted from the machine learning process may be converted to a suitable output format and transmitted or stored, as necessary.

The utterance analysis and prompt generation and output capabilities of the computer system 300 and other systems described herein may have application across a variety of fields. One particular field of application is medical consultation. In an embodiment, the computer system 300 can process audio of a medical consultation (e.g. between a doctor and a patient) and generate a prompt that suggests, recommends, or indicates a medical diagnosis for the patient based on the processed audio of the conversation. In another embodiment, the computer system 300 can process audio of a medical consultation and generate a prompt which suggests, recommends, or indicates one or more questions (e.g. a set of questions) to ask the patient and present the prompt to the information gatherer. The question determination process may use patient medical history data. In another embodiment, the computer system 300 can process audio of a medical consultation and generate a prompt which suggests, recommends, or indicates a potential side effect of a medication or medication exceptions based on patient medical history data or patient prescription data. Medication exceptions include medications that should not be used by or prescribed to the patient based on one or more factors, such as prior adverse reactions, adverse drug interactions, etc. In cases where the prompt generation process utilizes data other than audio data from the medical consultation in the analysis, such as patient medical history data and patient prescription data, such other data may be stored by or is otherwise accessible to the computer system 300 (e.g. in memory 302). The prompts may be generated and provided to a recipient device in real-time, such that the information gatherer can be prompted without significant interruptions in the consultation or without materially interrupting the flow of the conversation.

Figure 4:
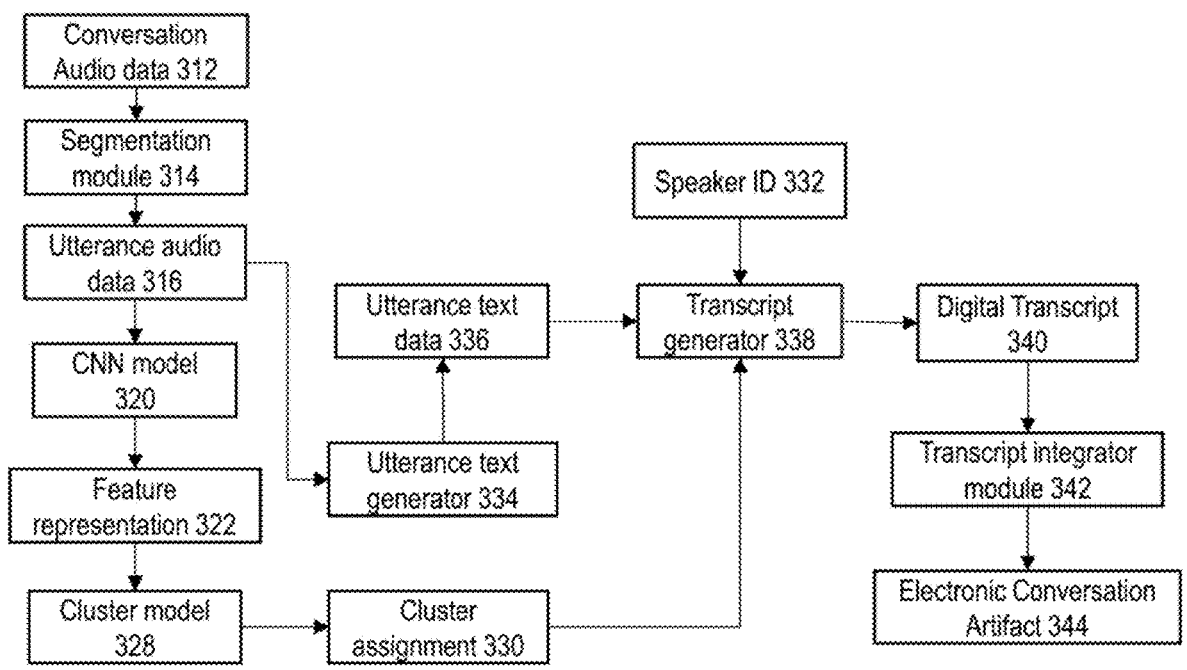
FIG. 4 is a flowchart of a pipeline for generating a digital transcript of a conversation using the system of FIG. 3, according to an embodiment.

Referring now to FIG. 4, shown therein is an example audio processing and transcription pipeline 400 carried out by the system 300 of FIG. 3, according to an embodiment. Aspects of the pipeline 400 are carried out by the audio processing server 12 of FIG. 1.

As shown, the pipeline 400 starts with conversation audio data 312. The conversation audio data 312 is a digital representation of a conversation between an information gatherer and an information provider. The conversation audio data 312 is generated by the audio capture device 16 and provided to the audio processing server 12 for processing.

The conversation audio data 316 is provided to the segmentation module 314, which generates utterance audio data 316 for a plurality of utterances.

The utterance audio data 316 is passed to the CNN model 320, which generates the feature representation 322.

The feature representation 322 is passed to the cluster model 328, which generates a cluster assignment 330 by assigning the feature representation 322, and the utterance represented thereby, to a cluster according to a clustering technique.

The utterance audio data is also passed to the utterance text generator 334, which generates utterance text data 336 comprising a text representation of the utterance.

The utterance text data 336, cluster assignment 330, and speaker ID 332 are passed to the transcript generator 338. The utterance text data includes time data 318 indicating the chronological position of the utterance in the conversation. The transcript generator arranges the text utterances 336 in chronological order using the time data 318 associated with the utterances. The transcript generator 338 assigns a speaker ID label 332 to each of the utterances based on the cluster assignment 330 for each utterance. The resulting conversation transcript 340 includes text of the utterances arranged in chronological order with each utterance attributed to a speaker according to the speaker ID 332.

The digital transcript 340 is passed to the transcript integrator module 342, which incorporates the digital transcript 340 (or an excerpt therefrom) into the electronic conversation artifact 344.

Figure 5:
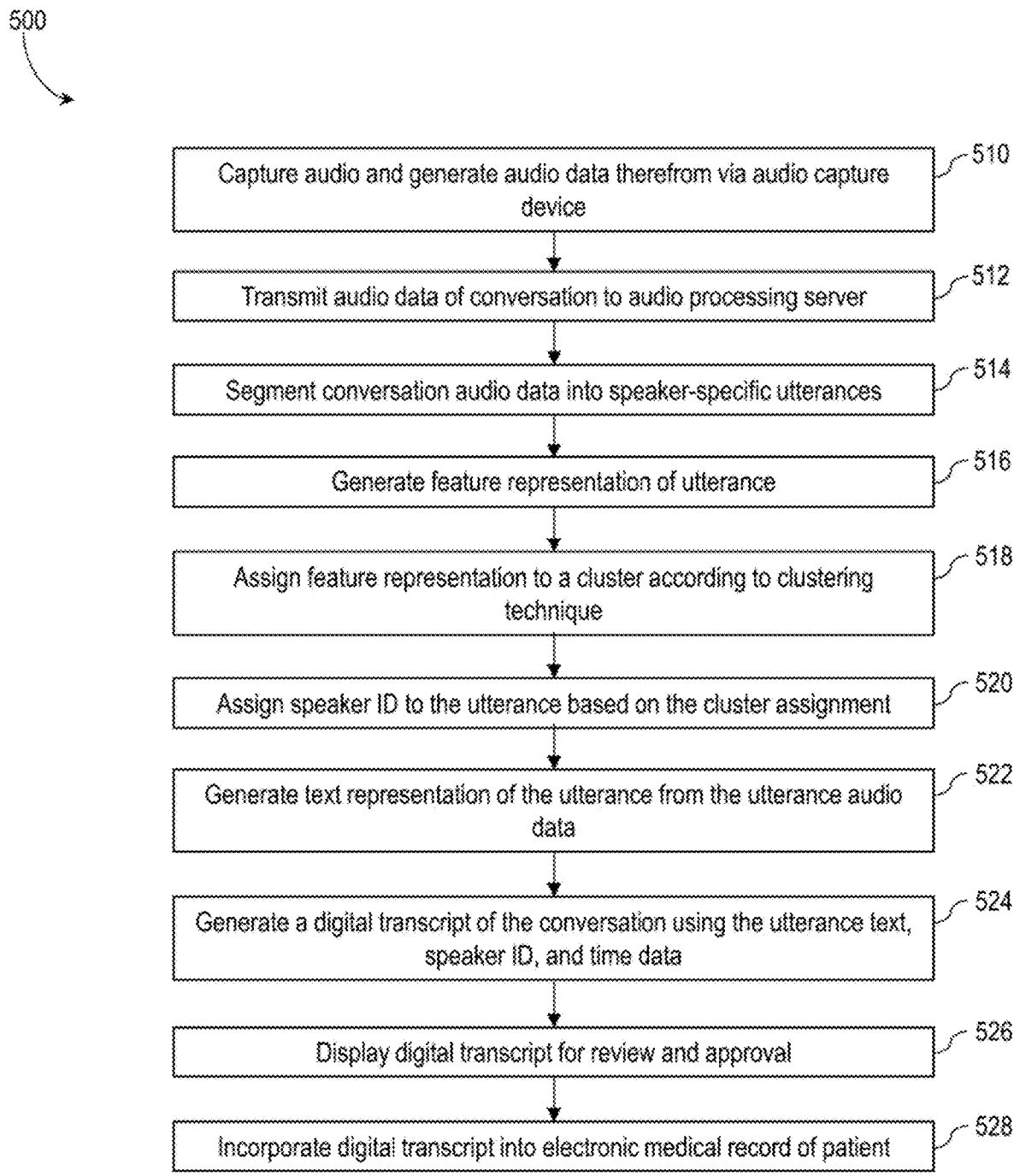
FIG. 5 is a flowchart of a method of generating a digital conversation transcript using the systems of the present disclosure in a medical consultation context, according to an embodiment.

Referring now to FIG. 5, shown therein is a method 500 of generating a transcript via the system 300 of Figure in a medical context, according to an embodiment. The medical context includes a patient visiting a physician for a consultation. The consultation includes a conversation between the patient and the physician wherein the patient is the information provider and the physician is the information gatherer.

Optionally, prior to the start of the conversation the physician may input speaker IDs 332. In an embodiment, this may include the physician inputting his name and the patient's name via the user interface 310 at the information gatherer device 18. In other cases, the speaker IDs 332 may be autopopulated according to an appointment record which includes a physician name and a patient name.

At 510, audio of the conversation between the physician and the patient is captured via the audio capture device 16 and conversation audio data 312 is generated therefrom.

At 512, the conversation audio data 312 is transmitted from the audio capture device 16 to the audio processing server 12 via the network 20.

At 514, the conversation audio data is segmented into speaker specific utterances 316 via the segmenter module 314. The speaker specific utterances 316 include patient utterances and physician utterances. In an example, a physician utterance may comprise a question, such as "do you have any pain?" and a patient utterance may comprise an answer to the question, such as "yes, I have been experiencing a shooting pain down my leg".

At 516, the utterance generated at 514 is passed to the neural network model 320 which generates the feature representation 322 of the utterance 316.

At 518, the feature representation 322 is passed to the cluster model 328. The cluster model 328 assigns the feature representation 322 to a cluster. The cluster label associated with the assigned cluster is assigned to the utterance on which the feature representation 322 is based. For example, physician utterances may be assigned to a first speaker cluster and patient utterances assigned to a second speaker cluster.

At 520, a speaker ID 332 is assigned to the utterance based on the cluster label applied to the feature representation 322. For example, utterances having a first speaker label assigned during clustering may be given a "Dr. Smith" speaker ID 332.

At 522, a text representation (utterance text data 336) of the utterance is generated using the utterance audio data 316 via the utterance text generator 334. The text representation may be generated prior to, during, or after the processing of the audio data via the neural network and cluster models 320, 328.

At 524, the transcript generator 338 generates a conversation transcript 340 using the utterance text 336 (and text representations of other utterances), speaker ID 332, and time data 318. The transcript includes utterances arranged in chronological order and attributed to either the physician or the patient.

At 526, the conversation transcript 340 is displayed at the information gatherer device 18 via the user interface 310. This allows the physician to review and confirm the transcript 340 and include any notes.

At 528, the conversation transcript 340 is incorporated into an electronic medical record (electronic artifact 340) for the patient. This may occur automatically upon the physician approving the transcript 340 at 526. In other cases, the physician may be presented with the option to import the transcript 340 into the EMR via a selectable icon or the like in the user interface 310.

Figure 6:
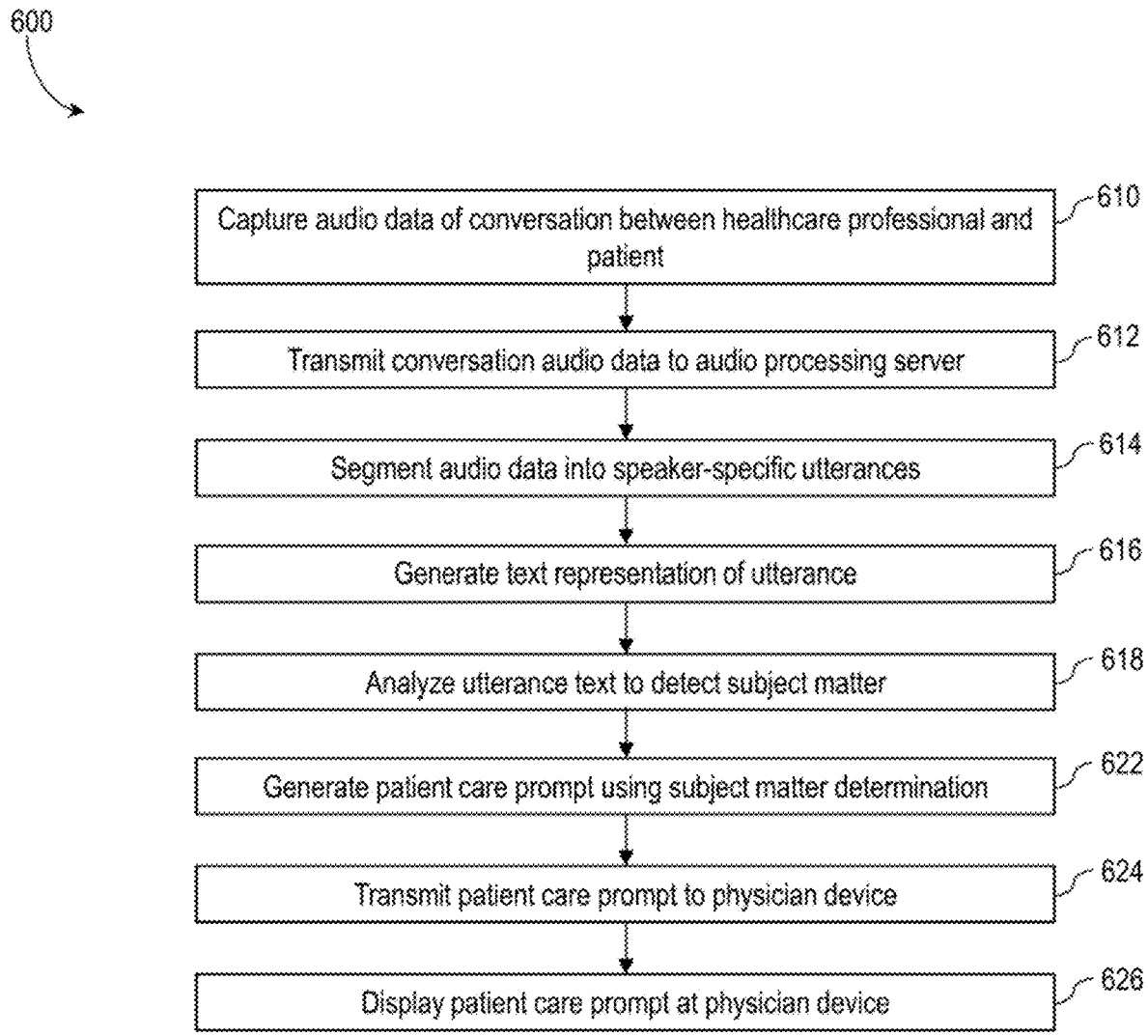
FIG. 6 is a flowchart of a method of generating and presenting real-time suggestions using the systems of the present disclosure in a medical consultation context, according to an embodiment.

Referring now to FIG. 6, shown therein is a method 600 of generating a subject matter prompt 352 via the system 300 of FIG. 3 in a medical context, according to an embodiment. The medical context includes a patient visiting a physician for a consultation. The consultation includes a conversation between the patient and the physician wherein the patient is the information provider and the physician is the information gatherer.

At 610, audio is captured of a conversation between a physician and a patient via the audio capture device 16. The audio capture device 16 generates audio data 312 representing the conversation.

At 612, the audio data 312 is transmitted to the audio processing server 12 via the network 20.

At 614, the audio data 312 is segmented into speaker specific utterances 316.

At 616, the utterances audio data 316 is processed into utterance text 336 via the utterance text generator 334.

At 618, the utterance text 336 is analyzed via the utterance analyzer 346. In some cases, the conversation transcript 340 may be generated and provided to the utterance analyzer 346.

The analysis of the utterance text may include some form of topic detection or text classification. For example, the utterance text may be analyzed and classified according to medical topic. Medical topics may include potential medical conditions. Topics may be detected based on the content of the conversation. The utterance analyzer 346 may analyze the utterance text and determine the conversation is about Condition X (i.e. subject matter determination 348).

At 622, the prompt generator 350 generates a patient care prompt 352 based on the subject matter determination 348. For example, the prompt 352 may be a condition X-specific prompt such as suggesting a specific prescription for condition X or a diagnosis of condition X. Prompts 352 may be stored and linked to the subject matter determinations 348.

At 624, the patient care prompt 352 is transmitted from the audio processing server 12 to the information gatherer device 18.

At 626, the patient care prompt 352 is displayed on the information gatherer device 18 via the user interface 310. In other cases, the prompt 352 may be or include an auditory prompt. In the medical context, a visual prompt on the physician device 18 may be more suitable so as to not alert the patient.

Specific embodiments of the systems of the present disclosure implementing a speaker clustering approach will now be described.

Speaker clustering is the task of segmenting available speaker utterances into speaker homogeneous sections or groupings (i.e. clusters).

Speaker clustering tasks include allocating the given speaker-specific utterances into a set of components, wherein each component contains utterances from a single speaker. The number of components should be equal to the number of unique speakers in the utterance set. The system is not aware of the identity of the speakers. It is called speaker diarization when the task of segmenting the audio stream into speaker-specific utterances is handled simultaneously.

Speaker Verification (SV), Speaker Identification (SI), and Audio Classification (AC) are some of the relevant problem domains to speaker clustering where some of the solution techniques can be fostered. Speaker Verification tasks include evaluating whether a voice utterance belongs to a given speaker or not. Speaker Identification tasks include identifying the correct speaker for an utterance. Audio Classification is a multiclass classification problem where a label out of n labels is added to a given audio recording. The imperceptibility regarding the identity and the number of speakers may make the speaker clustering problem a much more complex task than Speaker Verification, Speaker Identification, and Audio Classification. Speaker Verification, Speaker Identification, and Audio Classification are supervised problem domains, but speaker clustering is a completely unsupervised problem wherein the identity of speakers and the number of utterances per speaker is unknown.

Speaker Clustering is considered to be a prominent research area due to its potential usage in various tasks, domains, and application areas including conference/meeting minutes summarization, as a pre-processing step in automatic speech recognition, or as a component of an information retrieval system for audio archives. Further, Speaker Clustering may represent an abstract prototype for speaker diarization and may be a potential component in automated medical scribing systems, which intend to reduce the burden on human scribes.

Existing approaches have considered hand-crafted features and deep feature representations.

Traditionally, lower level feature extraction has been performed using Traditionally Mel Frequency Cepstral Coefficient (MFCC), Perceptual Linear Prediction (PLP), Line Spectral Frequencies (LSP), Pitch and the extracted features modelled using techniques such as Gaussian Mixture Models, Universal Background Model and i-vectors. Performance from directly clustering hand-crafted features using the above techniques has been shown to have a glass ceiling.

Figure 7:
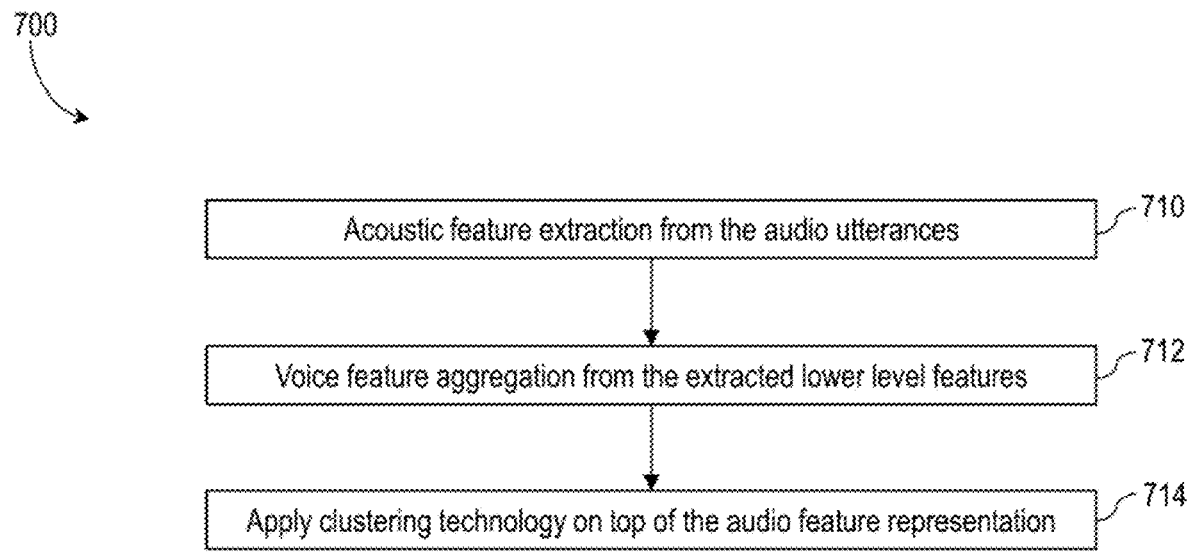
FIG. 7 is a flowchart of a speaker clustering pipeline, according to an embodiment.

Embodiments of the present disclosure may implement a speaker clustering pipeline, as shown in FIG. 7. The speaker clustering pipeline may be implemented by the audio processing server 12 of FIG. 1 or the computer system 300 of FIG. 3.

FIG. 7 illustrates speaker clustering pipeline 700, according to an embodiment. The speaker clustering pipeline 700 includes three stages. The input to the pipeline 700 includes audio utterances outputted by a segmentation process (e.g. utterance audio data 316 outputted via segmentation module 314 of FIG. 3).

At a first stage 710, an acoustic feature extraction process is applied to the audio utterances to generate lower level acoustic features.

At a second stage 712, voice feature aggregation via speaker modeling is performed on the extracted lower level features to generate a voice feature-based representation (e.g. feature representation 322 of FIG. 3).

Stages 710 and 712 may be performed via a neural network model such as CNN model (e.g. neural network model 320 of FIG. 3).

At a third stage 714, a clustering technology is applied to the voice feature-based representation to generate clustered utterances. The clustered utterances includes a cluster assignment wherein the assigned cluster includes speaker homogeneous utterances.

Referring now to FIG. 8, shown therein is a model architecture 800 of a CNN model for embedding extraction, according to an embodiment. The CNN model may be neural network model 320 of FIG. 3.

The CNN model is structured with a combination of convolutional and max-pooling layers with padding size 2×2, 3×3, respectively, followed by three fully connected layers with 4096, 4096, and 128 nodes, respectively.

The CNN model is a VGG model trained for large-scale audio classification tasks which differentiates 1000 classes of audios. VGG is a neural network model trained using Audioset with 1,010,480 random YouTube videos of 2,793.5 hours. It is an intuition that a model which is trained with this diverse set of acoustic database may have better generic speaker nuances than other generic audio embeddings.

The model of FIG. 8 may have an improved MR compared to existing models. Misclassification Rate (MR) may be used to evaluate the clustering performance. MR may be characterized by the following equation:

$$MR = \frac{1}{N} \sum_{j=1}^{N_c} e_j$$

N corresponds to the total number of utterances to be clustered, Nc to the number of speakers (=clusters) and ej to the number of incorrectly assigned utterances of speaker j. MR lies between 0 and 1 where 0 indicates the perfectly clustered utterances without any mis assignments to non-matching clusters and 1 correspond to the scenario where all the speaker utterances are clustered to false speakers.

Current embedding extraction approaches may have performance concerns. For example, experiments performed on current embedding extraction approaches show that their performance on same quality unseen data is not as expected as the audio feature representation from that model overfitted to the training data of TIMIT. of such models on unseen data. Further, it was identified that the extracted 512, 1024 feature dimensions include some non-relevant or redundant features by observing the same performance with reduced dimensions.

Embedding Extraction

One approach to improving model performance may include shifting focus to generic audio embeddings which can differentiate a wider range of voice characteristics and capture both acoustic and linguistic content.

Large-scale audio classification models including AlexNet, VGGish (slightly modified VGG), Inception, and ResNet may be potential candidates for the application of speaker clustering.

Out of these large-scale audio classification models, VGGish was selected. VGGish was trained using Audioset with 1,010,480 random YouTube videos of 2,793.5 hrs.

It is an intuition that a model which is trained with this diverse set of acoustic databases will have better generic speaker nuances compared to other generic audio embeddings.

Thus, we experimented with the VGGish model trained for large scale audio classification task which differentiates 1000 various acoustic classes.

We extracted the time series data of the audio utterance using a librosa library and extracted mel features from the audio utterance with a Fast Fourier Transform (FFT) window having a length of 25 ms and a window hop length of 10 ms.

The time series data may be an audio signal, denoted by y, and represented as a one-dimensional numpy.ndarray of floating-point values. y[t] corresponds to amplitude of the waveform at sample t.

The window may be a vector or function used to weight samples within a frame when computing a spectrogram. The frame may be a short slice of the time series used for analysis purposes which may correspond to a single column of a spectrogram matrix. The window length may be the length (width) of the window function (e.g., Hann window). The window length may be smaller than the frame length used in a short-time Fourier transform. The window length may be denoted as a positive integer variable win_length. The hop length may be the number of samples between successive frames, e.g., the columns of a spectrogram, and may be denoted as a positive integer hop_length.

From each window data 64 mel frequencies are extracted.

From the extracted embeddings, 960 ms data is gathered to create a two-dimensional frame (single spectrogram frame). The two-dimensional frame is used as the unit input for the convolutional VGG model. A frame may be a short slice of a time series used for analysis purpose and may correspond to a single column of a spectrogram matrix. The spectrogram may be a matrix S where the rows index frequency bins, and the columns index frames (time). Spectrograms may be either real-valued or complex-valued. By convention, real-valued spectrograms are denoted as numpy.ndarrays.

The pixel size of the single spectrogram frame is 64×96.

For a given utterance, the data is provided to the VGGish network as a batch of frames (a prepared spectrogram batch), where the number of frames is determined by the time length of the audio data.

The prepared spectrogram batch is provided as the input for the VGGish network and audio embeddings are extracted from all 13 layers of the network to identify the best embeddings layer which discriminates the speakers well.

From VCTK corpus, 40 speakers were randomly selected with ten utterances per speaker. Selected per speaker utterances were combined into two big utterances joining the first eight and last two utterances together so that the actual cluster contains two utterances per cluster. Finally, dominants sets clustering was applied on the embeddings using cosine as the distance metric and the clustering performance was measured using misclassification rate.

The VGGish model was evaluated with state of the art models VGGVox and RNN with TIMIT Small, TIMIT full, VCTK small, Noisy VCTK, and Sinhala ASR.

Misclassification Rate (MR) may be used to evaluate clustering performance according to the following equation:

$$MR = \frac{1}{N} \sum_{j=1}^{N_c} e_j.$$

N corresponds to the total number of utterances to be clustered.

Nc corresponds to the number of speakers (=clusters).

ej corresponds to the number of incorrectly assigned utterances of speaker J.

MR lies between 0 and 1, where 0 indicates that all utterances are perfectly clustered without any mis-assignments and 1 indicates that all utterances are assigned in correct clusters.

Referring now to architecture 800, the CNN includes a plurality of convolutional layers, max pooling layers, and fully connected layers.

The colored squares in the architecture 800 indicate the accuracy while FIG. 9, described below, shows the Misclassification rate, depicting the case that as the layer depth increases the MR is reduced while once it passes layer 828, then again MR goes up. So, FIG. 8 shows how Miscalculation rate is lower (the image depicts the inverse with the number of squares).

The convolutional layers include convolutional layers 810, 814, 818, 820, 824, and 826.

The max pooling layers include max pooling layers 812, 816, 822, and 828.

The fully connected layers include fully connected layers 830, 832, and 834.

Embeddings from all thirteen layers 810-834 of the CNN model 800 (VGGish model) were extracted and evaluated for the clustering performance.

For the fully connected layers 830, 832, 834, the two-dimensional embeddings were averaged over the vectors in a single batch.

For the max pooling layers 812, 816, 822, 828 and the convolutional layers 810, 814, 818, 820, 824, 826, the output embeddings were in 4 dimensions. Therefore, the embeddings were averaged over the frames in a single batch.

Figure 9:
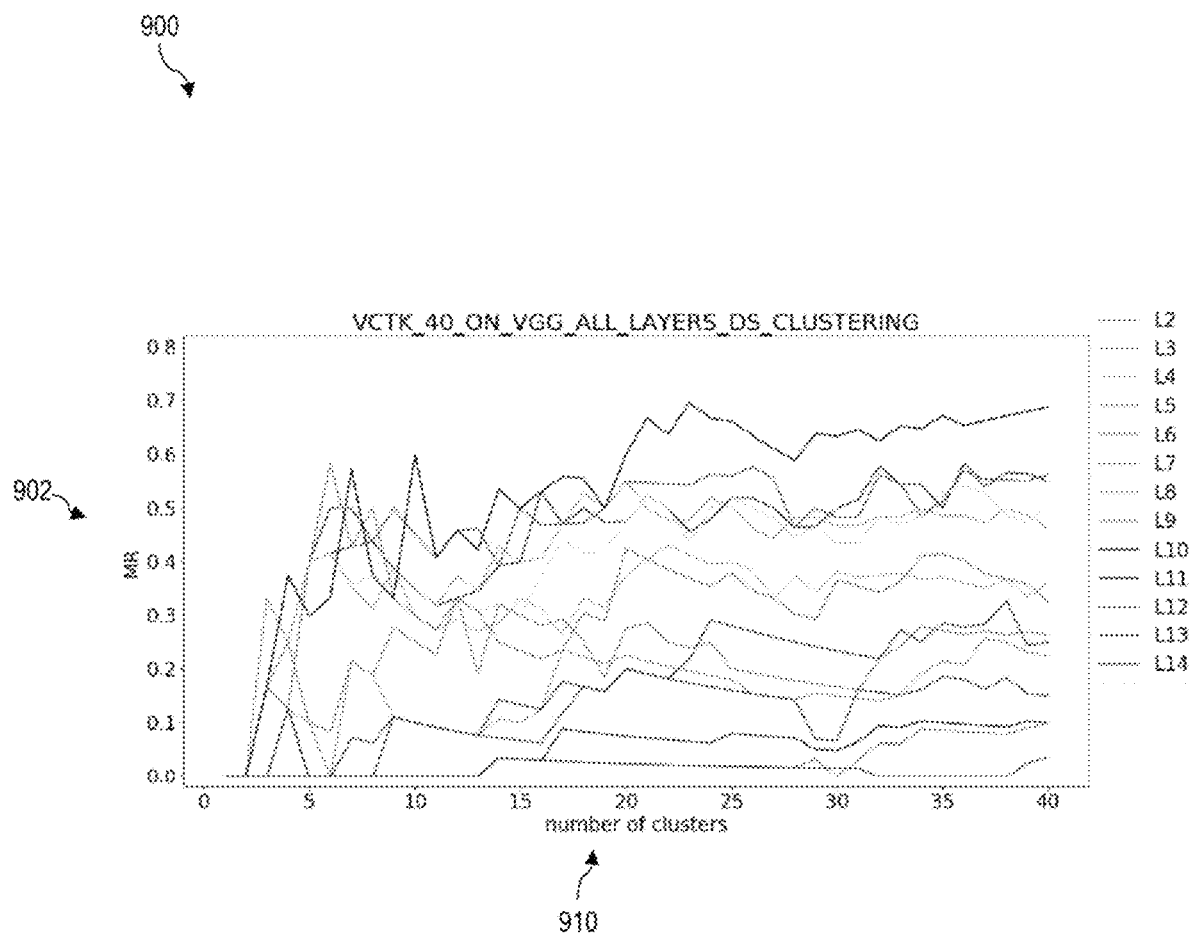
FIG. 9 is a graph showing a plot of miscalculation rate versus number of clusters for the layers of the CNN of the FIG. 8.

Referring now to FIG. 9, shown therein is a graph 900 showing performance of each embedding layer of the model 800 of FIG. 8 for the speaker clustering task. The graph 900 includes a horizontal axis 910 which represents the actual clusters in the selected data and a vertical axis 912 which represents the misclassification rate (MR) value.

The labels of the layers in graph 900 correspond to the network architecture 800 of FIG. 8. The layer L11 in graph 900 represents the clustering performance using the flattened embeddings of layer L10. As shown, as the layer is deeper, the MR is reduced and L10 is where the least MR, while as soon as you pass L10, MR becomes higher as you near L14.

The embeddings from top layers closely relate to the handcrafted mel features showing poor performance for the speaker clustering task. The top layers are the CNN layers that are near L1.

The embeddings from the bottom layers summarize the learning showing better performance for clustering. Bottom layers include the ones that are approaching to L10, where L10 is the most optimal and has the lowest MR.

When getting closer to the final softmax layer, the learning captures the information for the classification task and the performance deteriorates again.

The best performing embeddings extracted from the final max pool layer L10 (layer 128 of FIG. 8) with respect to the above argument. The softmax is the deepest layer (e.g. it may be the 13 or 14th layer), however the performance deteriorates shown by increased MR.

The CNN model 320 for speaker clustering described herein may provide competitive performance on different datasets.

Existing state-of-the-art approaches, such as RNN and VGGVox (VoxCeleb) may have an inability to distinguish unseen data.

The competitive performance of the VGGish embedding layer was verified on unseen data by testing the clustering performance on both TIM IT and VCTK corpus.

Table 1 shows the MR variation for TIMIT and VCTK for an embodiment of the CNN model of the present disclosure (VGGish trained using Audioset) compared to state-of-the-art VGGVox (VoxCeleb) and RNN models on unseen data from datasets including TIM IT small, TIMIT full, TIMIT full (k-means), VCTK small, Noisy VCTK, and Sinhala ASR:

| Datasets | RNN | VGGVox (VoxCeleb) | VGGish (Audioset) |
|---|---|---|---|
| TIMIT small | 0.04 | 0.0 | 0.0 |
| TIMIT full | 0.26 | 0.035 | 0.027 |
| TIMIT full (K-Means) | | | |
| VCTK Small | 0.20 | 0.04 | 0.01 |
| Noisy VCTK | 0.48 | | |
| Sinhala ASR | 0.614 | 0.521 | 0.512 |

As the number of speakers increases, the K-Means clustering may show better results than dominant sets after a threshold of 400 speakers. This emphasizes an intuition that with a very large number of speakers, DS clustering is miscalculating the speaker numbers while it performs significantly better compared to other approaches when the speakers are under 400.

Noise and Language Sensitivity Analysis

Table 2 below shows the performance of both VGGVox and VGGish in terms of MR on noisy data extracted from VoxCeleb according to geographical regions with minimum 30 speakers per region.

| Region/ | VGGVox | | | VGGish | | |
|---|---|---|---|---|---|---|
| Speakers | AHC | KM | DS | AHC | KM | DS |
| Aus (30) | 0.37 | 0.38 | 0.24 | 0.21 | 0.21 | 0.13 |
| USA (40) | 0.41 | 0.44 | 0.40 | 0.35 | 0.33 | 0.22 |
| UK (40) | 0.35 | 0.33 | 0.31 | 0.28 | 0.24 | 0.20 |
| Ca (40) | 0.31 | 0.26 | 0.26 | 0.24 | 0.22 | 0.18 |

As shown, the Dominant Sets (DS) clustering method proved to be better compared to agglomerative hierarchical clustering (AHC) and K-means (KM), due to its ability to identify the number of speakers when there is a small number of actual clusters available in the data. Furthermore, VGGish embeddings-based clustering is shown to be more robust against noisy environment and change of speaker accents. This may be supported by the ability of VGGish model to distinguish a wider range of voice characteristics.

Table 3 below shows testing of the language sensitivity of the models. As shown, better results were obtained for VGGish. It is not a significant improvement compared to VGGVox, but it is an improvement in terms of capturing acoustic features from different languages.

| Dataset | RNN | VGGVox (VoxCeleb) | VGGish (Audioset) |
|---|---|---|---|
| Sinhala ASR | 0.614 | 0.521 | 0.512 |
| Chinese dataset | 0.634 | 0.536 | 0.517 |

Proposed herein is a new deep audio embedding extraction mechanism for the speaker clustering pipeline. This method uses the application of transfer learning applied to a pre-trained AC model. It outperforms the VGGVox approach and other clustering techniques, and proved to be more robust against noisy utterances, accent variations and different languages. Further it is identified that the performance of a clustering algorithm may depend on the number of speakers and embeddings type. The speaker clustering performance was measured with noisy utterances, accent variations and language differences.

Features may include the application of various domain adaptation techniques to improve the performance of this method on noisy utterances, accent variations and language variations. Additional features may include scaling the number of utterances belonging to a unique speaker/cluster to match with real world use cases.

Datasets and data preparation techniques used for experiments used to test models described herein will now be described. Experiments were performed with a specific number of speakers from TIMIT dataset. The TIMIT dataset is composed of 6,300 phrases (10 phrases per speaker), spoken by 438 males (70%) and 192 females (30%) sampled at 16 kHz. Speakers coming from 8 different regions and having different dialects. Then VCTK speech data uttered by 109 native speakers of English with various accents where each speaker has 400 sentences was used. Data was sampled at 48 kHz.

For experimental purposes we used TIMIT small (40 Speakers), TIMIT full (630 Speakers) and VCTK small (40 Speakers) notations were used and followed the notation of Sinhala ASR for new dataset. We use VoxCeleb dataset was used to evaluate the embedding extraction mechanism against noisy data and speaker accent variation. To analyze the language sensitivity of the model, the models were evaluated using Sinhala language utterances from Sinhala Automated Speech Recognition (ASR) and Chinese mandarin datasets in Open Speech and Language Resources.

To ensure enough training data, 8 of the 10 sentences for each speaker were used for training. The remaining two sentences, corresponding to approximately 5 seconds, were used as test data.

In another embodiment, the systems of the present disclosure (e.g. computer system 300 of FIG. 3) include a speaker identification subsystem. The speaker identification subsystem may include one or more computer programs comprising computer-executable instructions that, when executed by a processor of the system (such as processor 304 of FIG. 3), cause the system to perform various speaker identification functions described herein.

The speaker identification subsystem may be implemented by an audio processing server, such as the audio processing server 12 of FIG. 1.

The speaker identification subsystem may be used to determine the identity of a speaker. In an example, the speaker identification subsystem may be configured to process audio of a conversation between a healthcare professional and a patient and determine an identity for the healthcare professional (e.g. Dr. Smith) and an identity for the patient (e.g. John Doe). The speaker identification subsystem may be used together with speaker clustering functionalities to provide improved audio processing and conversation transcript generation.

The speaker identification subsystem may include an end to end speaker model for speaker identification with minimal training.

In an embodiment, the speaker identification subsystem includes an attention-based LSTM model.

Details of various embodiments of the speaker identification subsystem will now be provided.

Deep learning has achieved good popularity and, in some cases, has outperformed GMM and i-vectors for speaker recognition. Neural network approaches have obtained promising results when fed by raw speech samples directly. A modified convolutional neural network (CNN) architecture called SincNet (referred to herein as "sincnet"), based on parameterized sinc functions, may offer a very compact way to derive a customized filter bank in short utterance. The filter bank is an array of band-pass filters that separates the input signal into multiple components. SincNet is based on parameterized Sinc functions, which is implemented using band-pass filters. Customized filter bank describes the Sinc function in sincnet.

The present disclosure provides an attention-based Long Short-Term Memory (LSTM) architecture that may enable discovery of more meaningful speaker-related features with minimal training. An attention layer built using neural network technology may offer a unique and efficient representation of the speaker characteristics explore the connection between an aspect and the content of short utterances. In order to identify the speaker in a system, the speech should represent unique characteristics. However, the previous methods include a lot of unrelated features in the speaker representations. In order to avoid the unrelated features in this mechanism, attention to the speaker-related features is needed. An attention layer built using neural network technology helps in achieving this task and helps to represent the speaker characteristics.

Experiments carried out on speaker identification tasks show that the proposed architecture may converge faster and perform better than sincnet.

Speaker identification includes classifying an identity of an unknown voice among a set of speakers. Speaker identification may have a broad scope on various research areas with application across many domains such as forensics, biometric authentication, speech recognition, and speaker diarization. Earlier state-of-the-art models include models based on the i-vector representation of speech segments, which offered significant advancements over previous Gaussian Mixture Model-Universal Background Models (GMMUBMs). Deep learning has provided success in various speech-related tasks, including recent research in speaker identification. Deep Neural Networks (DNNs) have been used within the i-vector framework to compute frame-level feature extraction.

DNNs have also been used as an end to end learning model for direct classification of speakers because of the elegant and brute force nature of deep learning. Even Though coefficients have been used in past research, there are no guarantees that such representations are optimal for all speech-related tasks because these engineered features are originally designed from perceptual evidence. Recent works reveal that CNN has been a successful architecture for processing raw speech samples, with CNN's built-in features such as weight distribution, local filters, and pooling helping the retrieval of robust and invariant representations. A restrained CNN architecture for speech recognition named sincnet, which includes of a set of parametrized sinc functions that implement band-pass filters, may ease the network to perform better than the previous speaker identification systems. It has been observed that sincnet comprehends the fine tuning on low-level feature extraction but did not study about the higher-level feature extraction. There are two types of feature extractions done in speaker identification tasks. The first is a low-level feature embedding extraction. The second is a high-level feature embedding extraction. Low-level feature extraction focuses on the extraction of acoustic information such as cepstral features and other voice parameters from raw audio. High-level feature extraction focuses on the extraction of phonetic, prosodic, or lexical information and other speaker-related characteristics. The output after a low-level feature extraction is fed as the input for high-level feature extraction. The SincNet methodology focuses on giving an effective low-level feature extraction means the scope is limited to low-level feature extraction. The filters learned by the sincnet may carry some incongruous multi-band shapes, especially when the number of training samples is very low. This representation makes some sense for the neural network but does not appear to be an efficient representation without higher-level feature fine-tuning of the speech signal, which may need some automatic feature selections from the clusters of features.

To help the sincnet discover more meaningful filters in the input layer, the present disclosure provides an approach which adds an attention-based LSTM layer to the sincnet implementation. This architecture may achieve better representation of the speech embeddings.

Compared to the sincnet model, where the low-level speech characteristics are well represented and convoluted with the waveform with a set of parametrized sinc functions that implement band-pass filters, a similar approach has been followed on the higher level using the attention layer. The attention layer may take each representation and give a weighted attention representation automatically. This solution may offer considerable flexibility and may force the network to concentrate only on the unique speaker characteristics with broad impact on the speaker identification task with minimal training. The use of the attention mechanism of the present disclosure may provide a way to search for the information related to the speaker and thus obtain better high-level embeddings, including better performance on speaker identification using the extracted embeddings. Further, the obtained higher-level embeddings are more discriminative than the existing model.

Experiments on this approach have been carried out under challenging but practical conditions, defined by minimal training data (e.g. 12-15 seconds for each speaker) and short test utterances (lasting from 2 to 6 seconds). Results obtained on two datasets show that the proposed attention-based LSTM achieves better accuracy on the speaker identification task than an existing state of the art model. Under the considered experimental setting, the architecture of the present disclosure also outperforms a more traditional speaker identification system based on i-vectors.

Details of the attention and LSTM layer architecture, according to an embodiment, will now be described.

Long Short-Term Memory (LSTM)

Recurrent neural network (RNN) is an extension of the standard feed-forward neural network. Long Short-Term Memory networks (called "LSTMs") are an enhanced version of RNN capable of learning long-term dependencies while avoiding gradient vanishing and exploding problems. The LSTM architecture includes three gates and a cell memory state.

Figure 10:
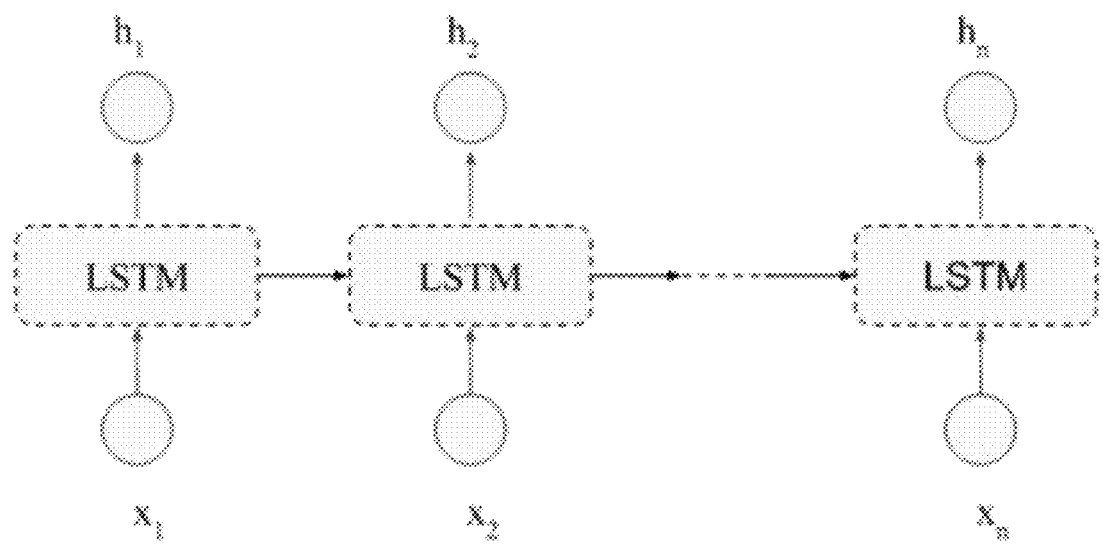
FIG. 10 is a schematic diagram of an architecture of a standard Long Short-term Memory ("LSTM")

Referring now to FIG. 10, shown therein is an architecture 1000 of a standard LSTM.

$\{x_1, x_2, \ldots f_n\}$ represents the low level features of an utterance.

$\{h_1, h_2, \ldots, h_n\}$ is the hidden vector.

Each Long short-term memory cell can be formed using the following equations:

$$X=[h_{t-1}, x_t] \quad (1)$$

$$f_t=\sigma(W_f \cdot \ldots X+b_f) \quad (2)$$

$$i_t=\sigma(W_i \cdot X+b_i) \quad (3)$$

$$o_t=\sigma(W_o \cdot X+b_o) \quad (4)$$

$$c_t=f_t \odot c_{t-1}+i_t \odot \tan h(W_c \cdot X+b_c) \quad (5)$$

$$h_t=o_t \odot \tan h(c_t) \quad (6)$$

The weights and the biases of the input, forget, and output gates $W_i, W_f, W_o \in \mathbb{R}^{d \times 2d}$ and $b_i, b_f, b_o \in \mathbb{R}^d$, respectively.

$\sigma$ is the sigmoid function and $\odot$ stands for element wise multiplication.

$x_t$ and $h_t$i are input and output hidden vectors, respectively.

Attention Layer with LSTM

The unidirectional LSTM cannot distinguish which is the essential part for speaker Identification. Bidirectional LSTMs are an extension of traditional LSTMs that can improve model performance on sequence classification problems. In speaker identification tasks, a speaker voice utterance can be considered a sequence of time-stamped events which makes speaker identification task a sequence classification problem (an utterance may contain a sequence of words). Unidirectional LSTM only learns in one direction at the same time. Bidirectional LSTM learns from forward and backwards. Bidirectional LSTM makes use of past data as well as future data, which helps tune the weights of the model in a way that the model can identify the essential part of speaker utterances. While bidirectional LSTM may provide efficient results as the bidirectional LSTM (or bi-LSTM) can understand context better, the bidirectional LSTM lacks on setting the unique features from the long dimensional feature vector. To address this issue, the present disclosure provides an attention mechanism that can grab a key part of speech features.

Figure 11:
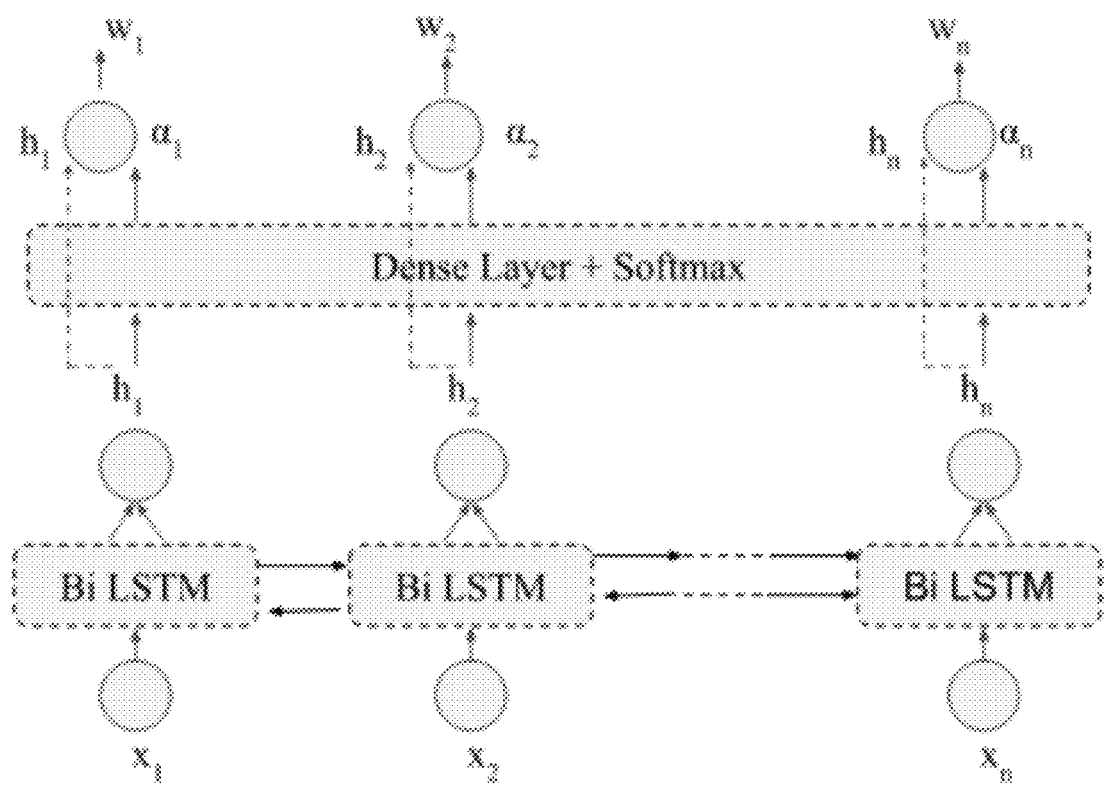
FIG. 11 is a schematic diagram of an architecture of an attention-based Bi-LSTM, according to an embodiment.

Referring now to FIG. 11, shown therein is an architecture 1100 of an attention-based Bi-LSTM, according to an embodiment. The attention-based Bi-LSTM may be used as part of a speaker identification subsystem of the present disclosure.

$\{\alpha_1, \alpha_2, \ldots, \alpha_n\}, \{w_1, w_2, \ldots, w_n\}$ represent the attention vectors and the utterance representations, respectively.

The attention mechanism produces an attention weight vector $\alpha$ and by multiplying the attention with the hidden vectors h produces the context vectors w. This procedure can be explained using the following equations:

$$h^t=<\vec{h}, \overleftarrow{h^t}> \quad (7)$$

$$w_t=h_t \times \alpha_t \quad (8)$$

These context vectors may better represent the most important part of utterances when different aspects are considered.

Several works have recently been explored in the speaker identification field. Deriving speaker-related characteristics from short utterances has been a difficult task throughout time. Development on deep learning such as DNN, CNN and LSTM, however, has helped significantly in selecting the unique features. Even though the i-vector system reduces the supervector dimension and effectively summarizes utterances, modified CNN architectures that utilize the sinc filters for time-domain audio processing from raw waveforms have been shown to outperform on both speaker identification tasks and speaker verification tasks. Studies show that sincnet may effectively summarize the raw audio form better than the MFCC and Raw CNN.

The architectures of the present disclosure may focus on higher-level speech embedding, which may only consider the needed features for the speaker identification tasks and may neglect the irrelevant characteristics for the context. Past works that use attention include machine translation, reasoning about entailment, and sentence summarization. The present disclosure explains the effectiveness of the proposed attention architecture on the speech identification domain on the realistic scenario characterized by a few seconds of training data for each speaker and short utterances for testing. One intention of the speaker identification task is to prove that it works well even on very small utterances because of the attention mechanism that is implemented on the model. In order to train the model, we need training data. The data is characterized by a few seconds of training data (the data used to train the model) for each speaker and short utterances for testing (the data used to test the model).

An experimental setup of the speaker identification subsystem will now be described.

The proposed architecture has been evaluated on different datasets and compared to various speaker identification baselines. In the spirit of reproducible research, we perform most experiments have been performed using publicly available data such as Librispeech and TIM IT.

An overview of the experimental settings will now be provided.

Datasets

To provide experimental proof on datasets characterized by different numbers of speakers, the present disclosure considers the TIMIT (462 speakers, train chunk) and Librispeech (2484 speakers) datasets.

The silence observed at the beginning and end of each utterance has been removed for the purposes of the experiments. Utterances observed with internal silences remaining more than 125 ms were split into multiple chunks.

Five sentences for each speaker were used for training, while the remaining three sentences were used for testing.

For the training and testing, tracks have been randomly picked to exploit 12-15 seconds of training tracks for each speaker and test utterances lasting 2-6 seconds.

Table 1 shows statistics of the dataset used for the speaker identification task.

| Dataset | Context | No of speakers |
| --- | --- | --- |
| LibriSpeech [21] | English speech | 921 |
| TIMIT [22] | English speech | 630 |

Low Level Feature Extraction

MFCC and sincnet were each used to extract the low-level features from the raw audio.

The raw audio data is processed. Processing may include includes splitting the waveform of each speech utterance (voice of speaker) into chunks with overlapping frames. For example, the waveform of each speech utterance may be split into chunks of 200 ms with 10 ms overlapping frames.

In a first experiment, the processed data was fed into the SincNet architecture. The results from this operation were fed into the proposed architecture of the present disclosure.

In a second experiment, the low-level features were extracted using the 0.25 ms with 10 ms overlap frames (i.e. to make the context the same (200 ms)) were used to generate 39 MFCCs (13 static coefficients, 13 delta coefficients, 13 delta-delta coefficients) each. As the MFCC feature vector describes only the power spectral envelope of a single frame, it seems like speech would also have information in the dynamics (e.g. what are the trajectories of the MFCC coefficients over time). It was determined that calculating the MFCC trajectories and appending them to the original feature vector increases ASR performance significantly (e.g. if there are 13 MFCC coefficients, we would also get 13 delta coefficients, 13 delta-delta coefficients which would combine to give a feature vector of length 39).

Table 2 shows experiments conducted on different low-level feature extraction models.

| | Experiment 1 | Experiment 2 |
| --- | --- | --- |
| Feature Extraction | MFCC [11] | SincNet [14] |
| Frame size | 25 ms | 20 ms |
| Type of processing | Traditional sound processing | Neutral architecture |

Attention Based LSTM Setup

The first standard Bidirectional layer performs a many-to-many encoding of the low-level features. This may generate a higher-dimensional output vector at the output layer from an input vector (e.g. sequence) through the application of functions (e.g. matrix multiply) to the input vector and other data generated therefrom.

The output of the bidirectional layer contains two hidden vectors for each cell, respectively.

A 128 (64*2) dimensional vector was passed through the attention mechanism. The attention weights for each vector are computed using the dense layer.

A neural network with 128 neurons computes the attentions and a softmax layer is used to normalize the sum of attention vectors to one.

The attention weights are then multiplied with the hidden state.

Frame-level speaker classification may be obtained by applying a softmax classifier which provides a set of posterior probabilities over the targeted speakers.

A sentence-level classification may be derived by averaging the frame predictions and voting for the speaker which maximizes the average posterior.

Training may use a Root mean square prop optimizer, with a learning rate of 0.001, alpha valued 0.95 and epsilon of 10-7, and mini-batches of size 128.

All the hyper-parameters of the architecture may be tuned on TIMIT dataset, and then inherited for Librispeech as well.

Baseline Setups

An embodiment of the architecture of the present disclosure was compared with several alternative systems.

First, Standard BI-LSTM was considered and fed using the methods explained above.

This network is also fed with the CNN SincNet-based feature extraction model.

A comparison with the popular low-level feature extraction mechanism was also performed.

Thirty-nine MFCCs (13 static coefficients, 13 delta coefficients, 13 delta-delta coefficients) and 40 FBANKs were computed using the LibROSA toolkit.

A CNN was used for FBANK features, while a Multi-Layer Perceptron (MLP) was used for MFCC.

Layer normalization was used for the FBANK network, while batch normalization was applied for the MFCC network.

The hyper-parameters of the FBANK and MFCC networks were also tuned using the previously researched procedures. Prior research suggests certain values for these parameters which are optimal for any research. These parameters are not tuned using the software but are done by a person.

The i-vector baseline was also examined.

The i-vector system was implemented with the SIDEKIT open-source toolkit.

The GMM-UBM model, the Total Variability (TV) matrix, and the Probabilistic Linear Discriminant Analysis (PLDA) were trained on the Librispeech data.

GMM-UBM was included 2048 Gaussians, and the rank of the TV and PLDA Eigen voice matrix was 400.

The enrollment and test phase is conducted on Librispeech using the same set of speech segments used for DNN experiments.

Results of the experiments will now be described.

The results provide an experimental validation of a proposed attention based Bi-LSTM layer of the present disclosure.

First, a comparison between the architecture of the present disclosure and the baseline standard BI-LSTM was performed.

Next, the architecture of the present disclosure was compared with other competitive systems on both speaker identification task.

Accuracy on experiments shows that the standard Bi-LSTM does not exhibit a meaningful accuracy compared to the architecture of the present disclosure. Experiments on the Attention-based Bidirectional LSTM model of the present disclosure have demonstrated improved accuracy over the baseline approach of Bidirectional LSTM model. This indicates that the proposed model provided an architecture for effectively representing the speaker which led to higher accuracy.

The attention mechanism of the architecture focuses on the unique characteristics and may be more selective than the Bi-LSTM (where it fails to learn the context). The proposed model is based on self-attention that implicitly focuses on the information outputted from the hidden layers of Bi-LSTM. However, Bi-LSTM itself includes no speaker-related data. To focus only on the speaker-related features, the attention mechanism is used.

Figure 12:
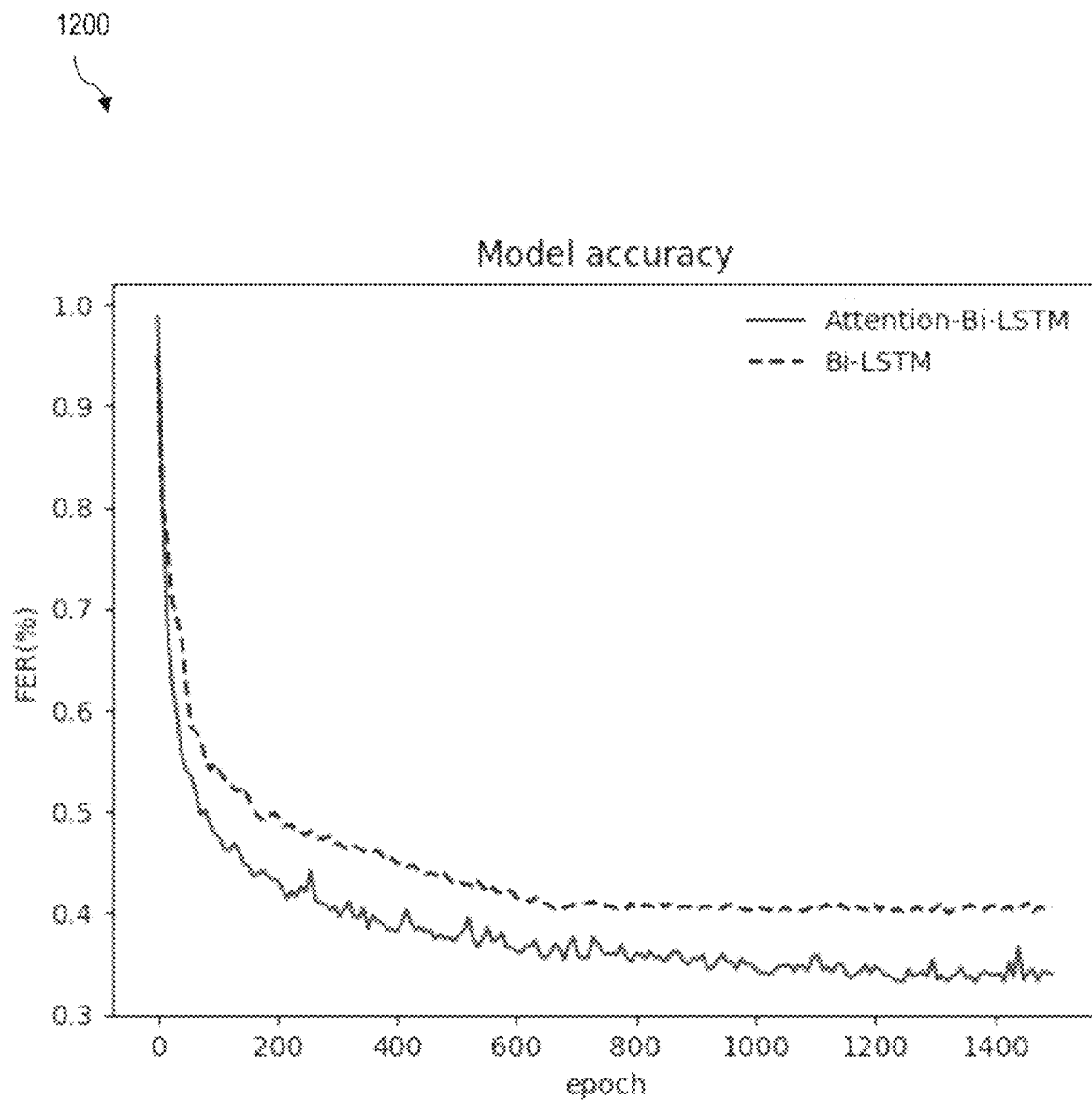
FIG. 12 is a graph showing learning curves of an attention-based Bidirectional LSTM ("Bi-LSTM") model of the present disclosure compared with a standard Bi-LSTM model.

FIG. 12 shows a plot 1200 of frame rate error (FMR) (%) of the Attention Bi-LSTM model of the present disclosure and the standard Bi-LSTM model over various training epochs. Results are from TIMIT dataset FIG. 12 shows learning curves of an Attention-based Bi-LSTM model of the present disclosure compared with a standard Bi-LSTM model. These results, achieved on the TIMIT dataset, highlight a faster decrease of the Frame Error Rate (FER %) when the Attention layer is used. Moreover, the Attention layer converges to better performance leading to a FER of 31.98% against a FER of 43.2% achieved with the Bi-LSTM baseline.

Table 3, provided below, shows Classification Error Rate (CER %) of speaker identification systems trained on TIM IT and Librispeech datasets. The Attention Bi-LSTM model of the present disclosure outperforms the competing alternatives.

|  | TIMIT | LibriSpeech |
| --- | --- | --- |
| DNN-MFCC | 0.99 | 2.02 |
| CNN-FBANK | 0.86 | 1.55 |
| SINCNET | 0.85 | 0.96 |
| Bi-LSTM | 0.94 | 1.32 |
| Sincnet Attention Bi-LSTM | 0 72 | 0.89 |
| MFCC Attention Bi-LSTM | 0.76 | 0.93 |

Table 3 reports the achieved Classification Error Rates (CER %).

Table 3 shows that the Attention Bi-LSTM model outperforms other systems on both TIMIT and Librispeech datasets, verifying the effectiveness of Attention-based Bi-LSTM with minimal training.

Regardless of the type of low-level feature extraction, the attention Bi-LSTM has been shown to achieve better accuracy not only with the sincnet architecture but also with the MFCC. Hence, standard Bi-LSTM models may be limited in their ability to represent the speaker embeddings correctly, while the attention-based Bi-LSTM of the present disclosure may perform well or better on those utterances with the help of the attention mechanism and aspect embedding.

The present disclosure provides a speaker identification subsystem includes an attention-based Bidirectional LSTM. The attention-based bidirectional LSTM includes a neural network architecture which may uniquely identify the speaker characteristics.

The attention-based Bidirectional LSTM model is inspired by the way the attention has been used on the machine translation in natural language processing field. The models of the present disclosure may learn unique characteristics and let aspects of the speaker utterances participate in computing attention weights.

The models of the present disclosure can focus on different parts of utterances when different aspects are given so that they are more competitive for unique speaker identification tasks. A critical and apparent disadvantage of this fixed-length context vector design (the out from the Bi-LSTM) is the incapability of the system to remember longer sequences. Often the earlier parts of the sequence are forgotten once the entire sequence has been processed. The attention mechanism described herein solves this problem. As a result, it can focus on different parts of utterances when different aspects are given so that they are more competitive for unique speaker identification tasks.

Experiments show that the speaker identification models of the present disclosure may provide superior performance over the baseline models.

In a further embodiment, the speaker identification model may include an attention mechanism such as in the attention-based bidirectional LSTM model and a temporal convolutional network ("TCN"). This may be advantageous given the TCN architecture can take a sequence of any length and map it to an output sequence of the same length, just as with an RNNs.

In yet further embodiments, variations of the speaker identification models described herein, such as the attention-based bidirectional LSTM model, may be used to process time-series and applied in other fields, such as speech recognition, emotion recognition, speech separation, and music processing. For example, variations of the models described herein may be used where a user is in a noisy background and with different recording devices.

While the above description provides examples of one or more apparatus, methods, or systems, it will be appreciated that other apparatus, methods, or systems may be within the scope of the claims as interpreted by one of skill in the art.

The invention claimed is:

1. A method of electronically documenting a conversation, the method comprising:
capturing audio of a conversation between a first speaker and a second speaker;
generating conversation audio data from the captured audio;
segmenting the conversation audio data into a plurality of audio utterances according to a speaker segmentation technique;
for each audio utterance:
storing time data indicating the chronological position of the audio utterance in the conversation;
passing the audio utterance as audio data to a neural network model, the neural network model configured to receive the audio utterance as an input and generate a feature representation of the audio utterance as an output;
assigning the audio utterance feature representation to a first speaker cluster or a second speaker cluster according to a clustering technique;
assigning a speaker identifier to the audio utterance based on the cluster assignment of the audio utterance;

generating a text representation of the audio utterance;
generating a digital transcript of the conversation by chronologically ordering the text representations of the audio utterances according to the time data for the audio utterances; and
importing the digital transcript into an electronic conversation artifact.

2. The method of claim 1, wherein the first speaker is a healthcare professional and the second speaker is a patient, and wherein the conversation is a medical consultation.

3. The method of claim 1, wherein the electronic conversation artifact is an electronic medical record.

4. The method of claim 1, wherein the neural network model includes a convolutional neural network.

5. A system for processing audio via speaker clustering, the system comprising:
an audio capture device configured to capture audio of a conversation between a first speaker and a second speaker and generate conversation audio data from the captured audio;
an audio processing server communicatively connected to the audio capture device, the audio processing server configured to:
receive the conversation audio data from the audio capture device;
segment the conversation audio data into a plurality of audio utterances, each audio utterance comprising utterance audio data, according to a segmentation technique; and
process the plurality of audio utterances via a speaker clustering pipeline, including:
passing each audio utterance to a neural network model, the neural network model configured to generate a feature representation of the audio utterance;
passing the audio utterance feature representation to a cluster model, the cluster model configured to assign the feature representation to a cluster based on speaker identity; and
storing the cluster assignment in a memory of the audio processing server.

6. The system of claim 5, wherein the audio processing server is further configured to generate a text representation of at least one audio utterance.

7. The system of claim 6, wherein the audio processing server is further configured to generate a digital transcript of the conversation including text representations of two or more audio utterances.

8. The system of claim 5, further comprising an information gatherer device communicatively connected to the audio processing server via a network, the information gatherer device configured to display the digital transcript for review by a user.

9. The system of claim 5, wherein upon approval of the digital transcript, the digital transcript is automatically imported into an electronic conversation artifact.

10. The system of claim 9, further comprising an electronic conversation artifact server communicatively connected to the audio processing server via the network, wherein the electronic artifact server is configured to generate and store the electronic conversation artifact.

11. The system of claim 5, wherein the neural network model is a VGGish model.

12. The system of claim 5, wherein the speaker clustering pipeline further includes extracting time series data of the utterance audio data.

13. The system of claim 5, wherein the speaker clustering pipeline further includes extracting mel features using an FFT window function.

14. The system of claim 12, wherein the utterance audio data is provided to the neural network model as a batch of spectrogram frames.

15. The system of claim 14, wherein the number of frames in the batch is determined by the time length of the utterance audio data.

16. The system of claim 5, wherein the cluster model implements a similarity function for determining the cluster assignment.

17. The system of claim 5, wherein the audio processing server comprises a speaker identification subsystem comprising a convolutional neural network and an attention-based LSTM layer.

18. The system of claim 17, wherein the convolutional neural network is SincNet.

* * * * *